United States Patent
Bouzek

(10) Patent No.: US 10,190,153 B2
(45) Date of Patent: Jan. 29, 2019

(54) METHODS FOR PREPARATION OF NUCLEIC ACID-CONTAINING SAMPLES USING CLAY MINERALS AND ALKALINE SOLUTIONS

(71) Applicant: Micronics, Inc., Redmond, WA (US)

(72) Inventor: Heather K. Bouzek, Seattle, WA (US)

(73) Assignee: MICRONICS, INC., Redmond, WA (US)

( * ) Notice: Subject to any disclaimer, the term of this patent is extended or adjusted under 35 U.S.C. 154(b) by 73 days.

(21) Appl. No.: 14/889,370

(22) PCT Filed: May 7, 2014

(86) PCT No.: PCT/US2014/037176
§ 371 (c)(1),
(2) Date: Nov. 5, 2015

(87) PCT Pub. No.: WO2014/182831
PCT Pub. Date: Nov. 13, 2014

(65) Prior Publication Data
US 2016/0102340 A1    Apr. 14, 2016

Related U.S. Application Data

(60) Provisional application No. 61/820,587, filed on May 7, 2013.

(51) Int. Cl.
| | |
|---|---|
| C12Q 1/68 | (2018.01) |
| C12Q 1/6806 | (2018.01) |
| C12N 15/10 | (2006.01) |
| C12Q 1/70 | (2006.01) |
| C07H 21/02 | (2006.01) |

(52) U.S. Cl.
CPC ....... C12Q 1/6806 (2013.01); C12N 15/1003 (2013.01); C12N 15/1006 (2013.01); C12Q 1/706 (2013.01); C12Q 1/707 (2013.01)

(58) Field of Classification Search
CPC ............ C12N 15/1003; C12N 15/1006; C12Q 1/6806; C12Q 1/706; C12Q 1/707
See application file for complete search history.

(56) References Cited

U.S. PATENT DOCUMENTS

| | | |
|---|---|---|
| 3,013,467 A | 12/1961 | Minsky |
| 3,799,742 A | 3/1974 | Coleman |
| 3,996,345 A | 12/1976 | Ullman et al. |
| 4,104,029 A | 8/1978 | Maier, Jr. |
| 4,235,960 A | 11/1980 | Sasse et al. |
| 4,304,257 A | 12/1981 | Webster |
| 4,366,241 A | 12/1982 | Tom et al. |
| 4,373,932 A | 2/1983 | Gribnau et al. |
| 4,610,678 A | 9/1986 | Weisman et al. |
| 4,683,195 A | 7/1987 | Mullis et al. |
| 4,683,202 A | 7/1987 | Mullis |
| 4,788,729 A | 12/1988 | Walker |
| 4,798,703 A | 1/1989 | Minekane |
| 4,800,159 A | 1/1989 | Mullis et al. |
| 4,810,630 A | 3/1989 | Craig et al. |
| 4,833,332 A | 5/1989 | Robertson, Jr. et al. |
| 4,837,168 A | 6/1989 | de Jaeger et al. |
| 4,848,722 A | 7/1989 | Webster |
| 4,855,240 A | 8/1989 | Rosenstein et al. |
| 4,869,282 A | 9/1989 | Sittler et al. |
| 4,883,750 A | 11/1989 | Whiteley et al. |
| 4,889,818 A | 12/1989 | Gelfand et al. |
| 4,943,522 A | 7/1990 | Eisinger et al. |
| 4,956,302 A | 9/1990 | Gordon et al. |
| 4,965,188 A | 10/1990 | Mullis et al. |
| 5,038,852 A | 8/1991 | Johnson et al. |
| 5,075,078 A | 12/1991 | Osikowicz et al. |
| 5,075,212 A | 12/1991 | Rotbart |
| 5,100,626 A | 3/1992 | Levin |
| 5,120,643 A | 6/1992 | Ching et al. |
| 5,130,238 A | 7/1992 | Malek et al. |
| 5,141,850 A | 8/1992 | Cole et al. |
| 5,145,578 A | 9/1992 | Tokubo et al. |
| 5,160,701 A | 11/1992 | Brown, III et al. |

(Continued)

FOREIGN PATENT DOCUMENTS

| | | |
|---|---|---|
| CN | 1146017 A | 3/1997 |
| CN | 1253625 A | 5/2000 |

(Continued)

OTHER PUBLICATIONS

Zhang, D. et al., Appl. Clay Sci., vol. 50, pp. 1-11 (2010).*

(Continued)

*Primary Examiner* — Teresa E Strzelecka
(74) *Attorney, Agent, or Firm* — Seed Intellectual Property Law Group LLP

(57) ABSTRACT

The present invention provides a rapid and highly effective method for the preparation of biological samples for detection of both DNA and RNA target molecules. The method comprises treatment of the sample with a clay mineral followed by lysis of the sample with an alkaline solution. The method is particularly suited for preparing complex biological samples, such as blood or plasma, for the simultaneous detection of DNA and RNA targets. Samples prepared by the method of the invention may be directly used as targets in PCR amplification. The method of the invention may conveniently be coupled with further steps and devices to perform molecular analyses for diagnostic and other applications.

19 Claims, 4 Drawing Sheets

(56) References Cited

U.S. PATENT DOCUMENTS

| | | |
|---|---|---|
| 5,192,980 A | 3/1993 | Dixon et al. |
| 5,225,163 A | 7/1993 | Andrews |
| 5,234,809 A | 8/1993 | Boom et al. |
| 5,252,459 A | 10/1993 | Tarcha et al. |
| 5,270,183 A | 12/1993 | Corbett et al. |
| 5,275,785 A | 1/1994 | May et al. |
| 5,296,703 A | 3/1994 | Tsien |
| 5,304,487 A | 4/1994 | Wilding et al. |
| 5,354,668 A | 10/1994 | Auerbach |
| 5,415,994 A | 5/1995 | Imrich et al. |
| 5,420,016 A | 5/1995 | Boguslaski et al. |
| 5,427,930 A | 6/1995 | Birkenmeyer et al. |
| 5,443,890 A | 8/1995 | Öhman |
| 5,447,440 A | 9/1995 | Davis et al. |
| 5,455,166 A | 10/1995 | Walker |
| 5,486,335 A | 1/1996 | Wilding et al. |
| 5,498,392 A | 3/1996 | Wilding et al. |
| 5,504,013 A | 4/1996 | Senior |
| 5,543,026 A | 8/1996 | Hoff et al. |
| 5,578,818 A | 11/1996 | Kain et al. |
| 5,582,989 A | 12/1996 | Caskey et al. |
| 5,587,128 A | 12/1996 | Wilding et al. |
| 5,591,645 A | 1/1997 | Rosenstein |
| 5,593,824 A | 1/1997 | Treml et al. |
| 5,602,040 A | 2/1997 | May et al. |
| 5,622,871 A | 4/1997 | May et al. |
| 5,631,734 A | 5/1997 | Stern et al. |
| 5,635,358 A | 6/1997 | Wilding et al. |
| 5,635,602 A | 6/1997 | Cantor et al. |
| 5,639,428 A | 6/1997 | Cottingham |
| 5,656,503 A | 8/1997 | May et al. |
| 5,658,723 A | 8/1997 | Oberhardt |
| 5,660,370 A | 8/1997 | Webster |
| 5,660,990 A | 8/1997 | Rao et al. |
| 5,670,381 A | 9/1997 | Jou et al. |
| 5,707,516 A | 1/1998 | Tomizawa et al. |
| 5,707,807 A | 1/1998 | Kato |
| 5,716,842 A | 2/1998 | Baier et al. |
| 5,716,852 A | 2/1998 | Yager et al. |
| 5,718,567 A | 2/1998 | Rapp et al. |
| 5,724,404 A | 3/1998 | Garcia et al. |
| 5,726,026 A | 3/1998 | Wilding et al. |
| 5,726,404 A | 3/1998 | Brody |
| 5,726,751 A | 3/1998 | Altendorf et al. |
| 5,730,850 A | 3/1998 | Kambara et al. |
| 5,747,349 A | 5/1998 | van den Engh et al. |
| 5,748,827 A | 5/1998 | Holl et al. |
| 5,759,014 A | 6/1998 | Van Lintel |
| 5,770,460 A | 6/1998 | Pawlak et al. |
| 5,798,273 A | 8/1998 | Shuler et al. |
| 5,856,174 A | 1/1999 | Lipshutz et al. |
| 5,863,502 A | 1/1999 | Southgate et al. |
| 5,863,801 A | 1/1999 | Southgate et al. |
| 5,872,710 A | 2/1999 | Kameyama |
| 5,906,602 A | 5/1999 | Weber et al. |
| 5,922,210 A | 7/1999 | Brody et al. |
| 5,922,591 A | 7/1999 | Anderson et al. |
| 5,932,100 A | 8/1999 | Yager et al. |
| 5,932,799 A | 8/1999 | Moles |
| 5,948,684 A | 9/1999 | Weigl et al. |
| 5,955,029 A | 9/1999 | Wilding et al. |
| 5,965,410 A | 10/1999 | Chow et al. |
| 5,971,158 A | 10/1999 | Yager et al. |
| 5,971,355 A | 10/1999 | Biegelsen et al. |
| 5,972,710 A | 10/1999 | Weigl et al. |
| 5,972,721 A | 10/1999 | Bruno et al. |
| 5,974,867 A | 11/1999 | Forster et al. |
| 5,989,813 A | 11/1999 | Gerdes |
| 6,001,307 A | 12/1999 | Naka et al. |
| 6,007,309 A | 12/1999 | Hartley |
| 6,007,775 A | 12/1999 | Yager |
| 6,018,616 A | 1/2000 | Schaper |
| 6,020,187 A | 2/2000 | Tam |
| 6,037,168 A | 3/2000 | Brown |
| 6,057,167 A | 5/2000 | Shieh et al. |
| 6,068,752 A | 5/2000 | Dubrow et al. |
| 6,086,740 A | 7/2000 | Kennedy |
| 6,158,712 A | 12/2000 | Craig |
| 6,168,948 B1 | 1/2001 | Anderson et al. |
| 6,171,865 B1 | 1/2001 | Weigl et al. |
| 6,184,029 B1 | 2/2001 | Wilding et al. |
| 6,210,514 B1 | 4/2001 | Cheung et al. |
| 6,210,882 B1 | 4/2001 | Landers et al. |
| 6,272,939 B1 | 8/2001 | Frye et al. |
| 6,287,850 B1 | 9/2001 | Besemer et al. |
| 6,303,389 B1 | 10/2001 | Levin et al. |
| 6,309,875 B1 | 10/2001 | Gordon |
| 6,325,975 B1 | 12/2001 | Naka et al. |
| 6,326,211 B1 | 12/2001 | Anderson et al. |
| 6,368,876 B1 | 4/2002 | Huang et al. |
| 6,387,290 B1 | 5/2002 | Brody et al. |
| 6,390,791 B1 | 5/2002 | Maillefer et al. |
| 6,399,398 B1 | 6/2002 | Cunningham et al. |
| 6,418,968 B1 | 7/2002 | Pezzuto et al. |
| 6,431,212 B1 | 8/2002 | Hayenga et al. |
| 6,439,036 B1 | 8/2002 | Mansky |
| 6,468,807 B1 | 10/2002 | Svensson et al. |
| 6,472,161 B1 | 10/2002 | Baugh |
| 6,488,896 B2 | 12/2002 | Weigl et al. |
| 6,506,346 B1 | 1/2003 | Monro |
| 6,541,213 B1 | 4/2003 | Weigl et al. |
| 6,541,274 B2 | 4/2003 | Nagle et al. |
| 6,562,209 B1 | 5/2003 | Sullivan et al. |
| 6,569,674 B1 | 5/2003 | McGarry et al. |
| 6,576,459 B2 | 6/2003 | Miles et al. |
| 6,581,899 B2 | 6/2003 | Williams |
| 6,614,030 B2 | 9/2003 | Maher et al. |
| 6,620,273 B2 | 9/2003 | Dai et al. |
| 6,632,655 B1 | 10/2003 | Mehta et al. |
| 6,635,487 B1 | 10/2003 | Lee et al. |
| 6,637,463 B1 | 10/2003 | Lei et al. |
| 6,664,104 B2 | 12/2003 | Pourahmadi et al. |
| 6,720,411 B2 | 4/2004 | Mirkin et al. |
| 6,729,352 B2 | 5/2004 | O'Connor et al. |
| 6,731,178 B2 | 5/2004 | Gailhard et al. |
| 6,731,781 B1 | 5/2004 | Shams et al. |
| 6,743,399 B1 | 6/2004 | Weigl et al. |
| 6,748,975 B2 | 6/2004 | Hartshorne et al. |
| 6,758,107 B2 | 7/2004 | Cabuz |
| 6,767,194 B2 | 7/2004 | Jeon et al. |
| 6,787,338 B2 | 9/2004 | Wittwer et al. |
| 6,793,753 B2 | 9/2004 | Unger et al. |
| 6,815,160 B1 | 11/2004 | Chien et al. |
| 6,843,263 B2 | 1/2005 | Kuo et al. |
| 6,872,566 B2 | 3/2005 | Vischer et al. |
| 6,901,949 B2 | 6/2005 | Cox et al. |
| 6,916,113 B2 | 7/2005 | Van de Goor et al. |
| 6,951,632 B2 | 10/2005 | Unger et al. |
| 6,953,675 B2 | 10/2005 | Leung et al. |
| 6,953,676 B1 | 10/2005 | Wilding et al. |
| 6,955,738 B2 | 10/2005 | Derand et al. |
| 6,974,119 B2 | 12/2005 | Brendle et al. |
| 6,974,669 B2 | 12/2005 | Mirkin et al. |
| 7,010,391 B2 | 3/2006 | Handique et al. |
| 7,052,594 B2 | 5/2006 | Pelrine et al. |
| 7,087,414 B2 | 8/2006 | Gerdes et al. |
| 7,141,416 B2 | 11/2006 | Krutzik |
| 7,153,673 B2 | 12/2006 | Stern |
| 7,223,363 B2 | 5/2007 | McNeely et al. |
| 7,223,371 B2 | 5/2007 | Hayenga et al. |
| 7,226,562 B2 | 6/2007 | Holl et al. |
| 7,235,400 B2 | 6/2007 | Adey |
| 7,318,913 B2 | 1/2008 | Loeffler et al. |
| 7,416,892 B2 | 8/2008 | Battrell et al. |
| 7,445,926 B2 | 11/2008 | Mathies et al. |
| 7,514,212 B2 | 4/2009 | Prudent et al. |
| 7,517,651 B2 | 4/2009 | Marshall et al. |
| 7,541,147 B2 | 6/2009 | Marshall et al. |
| 7,544,506 B2 | 6/2009 | Breidford et al. |
| 7,607,641 B1 | 10/2009 | Yuan |
| 7,615,370 B2 | 11/2009 | Streit et al. |
| 7,648,835 B2 | 1/2010 | Breidford et al. |
| 7,695,683 B2 | 4/2010 | Quan et al. |
| 7,749,444 B2 | 7/2010 | Yamada et al. |

(56) References Cited

U.S. PATENT DOCUMENTS

| | | |
|---|---|---|
| 7,763,453 B2 | 7/2010 | Clemmens et al. |
| 7,785,776 B2 | 8/2010 | Wittwer et al. |
| 7,832,429 B2 | 11/2010 | Young et al. |
| 7,906,317 B2 | 3/2011 | Lee et al. |
| 7,955,836 B2 | 6/2011 | Clemmens et al. |
| 8,104,497 B2 | 1/2012 | Unger et al. |
| 8,104,514 B2 | 1/2012 | Fernandes et al. |
| 8,110,392 B2 | 2/2012 | Battrell et al. |
| 8,222,023 B2 | 7/2012 | Battrell et al. |
| 8,329,453 B2 | 12/2012 | Battrell et al. |
| 8,431,389 B2 | 4/2013 | Battrell et al. |
| 8,716,007 B2 | 5/2014 | Battrell et al. |
| 8,747,779 B2 | 6/2014 | Sprague et al. |
| 8,772,017 B2 | 7/2014 | Battrell et al. |
| 9,056,291 B2 | 6/2015 | Battrell et al. |
| 9,132,423 B2 | 9/2015 | Battrell et al. |
| 9,272,280 B2 | 3/2016 | Viola et al. |
| 2001/0046701 A1 | 11/2001 | Schulte et al. |
| 2002/0081934 A1 | 6/2002 | Murao et al. |
| 2002/0086443 A1 | 7/2002 | Bamdad |
| 2002/0137196 A1 | 9/2002 | Miles et al. |
| 2002/0160518 A1 | 10/2002 | Hayenga et al. |
| 2002/0192676 A1 | 12/2002 | Madonna et al. |
| 2002/0195152 A1 | 12/2002 | Fernandes et al. |
| 2003/0008308 A1 | 1/2003 | Enzelberger et al. |
| 2003/0013184 A1 | 1/2003 | Streit et al. |
| 2003/0032028 A1 | 2/2003 | Dace et al. |
| 2003/0073229 A1 | 4/2003 | Greenstein et al. |
| 2003/0124619 A1 | 7/2003 | Weigl et al. |
| 2003/0129756 A1 | 7/2003 | Thorne et al. |
| 2003/0136178 A1 | 7/2003 | Cabuz |
| 2003/0152927 A1 | 8/2003 | Jakobsen et al. |
| 2003/0152994 A1 | 8/2003 | Woudenberg et al. |
| 2003/0153686 A1 | 8/2003 | Onoe et al. |
| 2003/0175990 A1 | 9/2003 | Hayenga et al. |
| 2003/0215818 A1 | 11/2003 | Lorenz |
| 2003/0215825 A1 | 11/2003 | Tong |
| 2003/0224434 A1 | 12/2003 | Wittwer et al. |
| 2004/0005718 A1 | 1/2004 | Fukushima |
| 2004/0018611 A1 | 1/2004 | Ward et al. |
| 2004/0024051 A1 | 2/2004 | Holton |
| 2004/0037739 A1 | 2/2004 | McNeely et al. |
| 2004/0081997 A1 | 4/2004 | Stern |
| 2004/0115094 A1 | 6/2004 | Gumbrecht et al. |
| 2004/0121364 A1 | 6/2004 | Chee et al. |
| 2004/0124384 A1 | 7/2004 | Biegelsen et al. |
| 2004/0189311 A1 | 9/2004 | Glezer et al. |
| 2004/0209354 A1 | 10/2004 | Mathies et al. |
| 2004/0224339 A1 | 11/2004 | Numajiri et al. |
| 2004/0226348 A1 | 11/2004 | Bruce, III et al. |
| 2004/0248167 A1 | 12/2004 | Quake et al. |
| 2005/0013732 A1 | 1/2005 | Battrell et al. |
| 2005/0019792 A1 | 1/2005 | McBride et al. |
| 2005/0019898 A1 | 1/2005 | Adey et al. |
| 2005/0037397 A1 | 2/2005 | Mirkin et al. |
| 2005/0106066 A1 | 5/2005 | Saltsman et al. |
| 2005/0106742 A1 | 5/2005 | Wahl |
| 2005/0118570 A1 | 6/2005 | Hollis et al. |
| 2005/0129582 A1 | 6/2005 | Breidford et al. |
| 2005/0136552 A1 | 6/2005 | Buechler |
| 2005/0142582 A1 | 6/2005 | Doyle et al. |
| 2005/0157301 A1 | 7/2005 | Chediak et al. |
| 2005/0161669 A1 | 7/2005 | Jovanovich et al. |
| 2005/0164373 A1 | 7/2005 | Oldham et al. |
| 2005/0186585 A1 | 8/2005 | Juncosa et al. |
| 2005/0205816 A1 | 9/2005 | Hayenga et al. |
| 2005/0217741 A1 | 10/2005 | Bohm |
| 2005/0221281 A1 | 10/2005 | Ho |
| 2005/0284817 A1 | 12/2005 | Fernandez et al. |
| 2006/0003440 A1 | 1/2006 | Streit et al. |
| 2006/0073484 A1 | 4/2006 | Mathies et al. |
| 2006/0076068 A1 | 4/2006 | Young et al. |
| 2006/0127886 A1 | 6/2006 | Kaylor et al. |
| 2006/0166375 A1 | 7/2006 | Hawkins et al. |
| 2006/0178568 A1 | 8/2006 | Danna et al. |
| 2006/0246575 A1 | 11/2006 | Lancaster et al. |
| 2006/0254916 A1 | 11/2006 | Hernandez et al. |
| 2006/0263816 A1 | 11/2006 | Laikhter et al. |
| 2006/0264782 A1 | 11/2006 | Holmes et al. |
| 2006/0275852 A1 | 12/2006 | Montagu et al. |
| 2006/0275893 A1 | 12/2006 | Ishii et al. |
| 2006/0292588 A1 | 12/2006 | Chou et al. |
| 2006/0292630 A1 | 12/2006 | Fukumoto |
| 2007/0008536 A1 | 1/2007 | Mitani et al. |
| 2007/0009383 A1 | 1/2007 | Bedingham et al. |
| 2007/0014695 A1 | 1/2007 | Yue et al. |
| 2007/0042427 A1 | 2/2007 | Gerdes et al. |
| 2007/0125947 A1 | 6/2007 | Sprinzak et al. |
| 2007/0154895 A1 | 7/2007 | Spaid et al. |
| 2007/0183935 A1 | 8/2007 | Clemmens et al. |
| 2007/0190525 A1 | 8/2007 | Gu et al. |
| 2007/0219366 A1 | 9/2007 | Gumbrecht et al. |
| 2007/0234785 A1 | 10/2007 | Beerling et al. |
| 2007/0243603 A1 | 10/2007 | Einsle et al. |
| 2007/0280856 A1 | 12/2007 | Ulmanella et al. |
| 2007/0292858 A1 | 12/2007 | Chen et al. |
| 2008/0050283 A1 | 2/2008 | Chou et al. |
| 2008/0081341 A1 | 4/2008 | Maher et al. |
| 2008/0124749 A1 | 5/2008 | Farnam et al. |
| 2008/0226500 A1 | 9/2008 | Shikida et al. |
| 2008/0260586 A1 | 10/2008 | Boamfa |
| 2008/0274511 A1 | 11/2008 | Tan et al. |
| 2008/0297792 A1 | 12/2008 | Kim et al. |
| 2009/0000678 A1 | 1/2009 | Therriault et al. |
| 2009/0017483 A1 | 1/2009 | Yamaoka et al. |
| 2009/0047713 A1 | 2/2009 | Handique |
| 2009/0061450 A1 | 3/2009 | Hunter |
| 2009/0111159 A1 | 4/2009 | Brolaski et al. |
| 2009/0148847 A1 | 6/2009 | Kokoris et al. |
| 2009/0148933 A1 | 6/2009 | Battrell et al. |
| 2009/0181411 A1 | 7/2009 | Battrell et al. |
| 2009/0298059 A1 | 12/2009 | Gumbrecht et al. |
| 2009/0325203 A1 | 12/2009 | Jenny et al. |
| 2009/0325276 A1 | 12/2009 | Battrell et al. |
| 2010/0041049 A1 | 2/2010 | Smith et al. |
| 2010/0112723 A1 | 5/2010 | Battrell et al. |
| 2010/0120129 A1 | 5/2010 | Amshey et al. |
| 2010/0291588 A1 | 11/2010 | McDevitt et al. |
| 2010/0303687 A1 | 12/2010 | Blaga et al. |
| 2011/0151479 A1 | 6/2011 | Stevens et al. |
| 2011/0207621 A1 | 8/2011 | Montagu et al. |
| 2012/0028342 A1 | 2/2012 | Ismagilov et al. |
| 2012/0064597 A1 | 3/2012 | Clemmens et al. |
| 2012/0071342 A1 | 3/2012 | Lochhead et al. |
| 2012/0115214 A1 | 5/2012 | Battrell et al. |
| 2012/0135511 A1 | 5/2012 | Battrell et al. |
| 2012/0156750 A1 | 6/2012 | Battrell et al. |
| 2012/0164383 A1 | 6/2012 | Sollmann |
| 2012/0164627 A1 | 6/2012 | Battrell et al. |
| 2012/0177543 A1 | 7/2012 | Battrell et al. |
| 2012/0329142 A1 | 12/2012 | Battrell et al. |
| 2013/0011912 A1 | 1/2013 | Battrell et al. |
| 2013/0017552 A1 | 1/2013 | Rudorfer |
| 2013/0032235 A1 | 2/2013 | Johnstone et al. |
| 2013/0130262 A1 | 5/2013 | Battrell et al. |
| 2014/0349381 A1 | 11/2014 | Battrell et al. |
| 2015/0158026 A1 | 6/2015 | Battrell et al. |
| 2015/0321193 A1 | 11/2015 | Sprague et al. |
| 2015/0346097 A1 | 12/2015 | Battrell et al. |
| 2015/0352549 A1 | 12/2015 | Kolb et al. |
| 2016/0090588 A1 | 3/2016 | Lofquist et al. |
| 2016/0102340 A1 | 4/2016 | Bouzek |
| 2016/0193603 A1 | 7/2016 | Battrell et al. |
| 2017/0113221 A1 | 4/2017 | Hoffman et al. |

FOREIGN PATENT DOCUMENTS

| | | |
|---|---|---|
| CN | 102602087 A | 7/2012 |
| DE | 20 2004 012 163 U1 | 11/2004 |
| EP | 0 320 308 A2 | 6/1989 |
| EP | 0 329 822 A2 | 8/1989 |
| EP | 0 517 631 A1 | 12/1992 |
| EP | 1 180 135 B1 | 8/2005 |
| EP | 1 659 405 A1 | 5/2006 |

(56) References Cited

FOREIGN PATENT DOCUMENTS

| | | |
|---|---|---|
| EP | 1 707 965 A1 | 10/2006 |
| EP | 1 726 940 A1 | 11/2006 |
| EP | 1 792 654 A2 | 6/2007 |
| GB | 2 202 328 A | 9/1988 |
| JP | 52-55679 A | 5/1977 |
| JP | 61-137066 A | 6/1986 |
| JP | 7-151101 A | 6/1995 |
| JP | 2520468 Y2 | 9/1996 |
| JP | 10-82773 A | 3/1998 |
| JP | 10-504916 A | 5/1998 |
| JP | 11-508347 A | 7/1999 |
| JP | 2000-314719 A | 11/2000 |
| JP | 2003-166910 A | 6/2003 |
| JP | 2003-207454 A | 7/2003 |
| JP | 2004-028589 A | 1/2004 |
| JP | 2004-333452 A | 11/2004 |
| JP | 2005-512071 A | 4/2005 |
| JP | 2005/088280 A1 | 9/2005 |
| JP | 2005-527303 A | 9/2005 |
| JP | 2005-531006 A | 10/2005 |
| JP | 2005-345378 A | 12/2005 |
| JP | 2006-84459 A | 3/2006 |
| JP | 2006-90774 A | 4/2006 |
| JP | 2006-512092 A | 4/2006 |
| JP | 2006-122743 A | 5/2006 |
| JP | 2006-517029 A | 7/2006 |
| JP | 2006-227301 A | 8/2006 |
| JP | 2006-246777 A | 9/2006 |
| JP | 2006-520190 A | 9/2006 |
| JP | 2007-514142 A | 5/2007 |
| JP | 2007/137291 A1 | 11/2007 |
| JP | 2007-532918 A | 11/2007 |
| JP | 2008-503722 A | 2/2008 |
| JP | 2008-89597 A | 4/2008 |
| JP | 2008-96375 A | 4/2008 |
| JP | 2008-537063 A | 9/2008 |
| JP | 2009-14529 A | 1/2009 |
| JP | 2009-019962 A | 1/2009 |
| JP | 2009-510337 A | 3/2009 |
| JP | 2009-513966 A | 4/2009 |
| JP | 2009-529883 A | 8/2009 |
| JP | 2009-255083 A | 11/2009 |
| JP | 2010-78508 A | 4/2010 |
| JP | 2010-519463 A | 6/2010 |
| JP | 2010-535346 A | 11/2010 |
| JP | 2012-516455 A | 7/2012 |
| JP | 2013-518289 A | 5/2013 |
| JP | 2015-510111 A | 4/2015 |
| JP | 2016-508197 A | 3/2016 |
| WO | 86/06488 A1 | 11/1986 |
| WO | 88/08534 A1 | 11/1988 |
| WO | 88/10315 A1 | 12/1988 |
| WO | 89/06700 A1 | 7/1989 |
| WO | 89/09284 A1 | 10/1989 |
| WO | 91/12336 A1 | 8/1991 |
| WO | 96/33399 A1 | 10/1996 |
| WO | 97/01055 A1 | 1/1997 |
| WO | 98/49543 A1 | 11/1998 |
| WO | 00/63670 A1 | 10/2000 |
| WO | 01/070381 A2 | 9/2001 |
| WO | 02/001184 A1 | 1/2002 |
| WO | 02/012896 A1 | 2/2002 |
| WO | 02/041994 A2 | 5/2002 |
| WO | 02/072262 A1 | 9/2002 |
| WO | 02/081934 A2 | 10/2002 |
| WO | 03/015923 A1 | 2/2003 |
| WO | 03/031977 A2 | 4/2003 |
| WO | 03/049860 A1 | 6/2003 |
| WO | 03/054523 A2 | 7/2003 |
| WO | 03/097831 A1 | 11/2003 |
| WO | 03/099355 A2 | 12/2003 |
| WO | 03/101887 A2 | 12/2003 |
| WO | 03/102546 A2 | 12/2003 |
| WO | 2004/055198 A2 | 7/2004 |
| WO | 2004/061085 A2 | 7/2004 |
| WO | 2004/065010 A2 | 8/2004 |
| WO | 2004/065930 A2 | 8/2004 |
| WO | 2005/016529 A1 | 2/2005 |
| WO | 2005/022154 A1 | 3/2005 |
| WO | 2005/066638 A1 | 7/2005 |
| WO | 2005/069015 A1 | 7/2005 |
| WO | 2005/106024 A2 | 11/2005 |
| WO | 2005/118849 A1 | 12/2005 |
| WO | 2006/018811 A1 | 2/2006 |
| WO | 2006/035830 A1 | 4/2006 |
| WO | 2006/052652 A2 | 5/2006 |
| WO | 2006/076567 A2 | 7/2006 |
| WO | 2006/083833 A2 | 8/2006 |
| WO | 2006/025767 A1 | 11/2006 |
| WO | 2007/049009 A1 | 5/2007 |
| WO | 2007/064635 A1 | 6/2007 |
| WO | 2007/106579 A2 | 9/2007 |
| WO | 2007/106580 A2 | 9/2007 |
| WO | 2007/109584 A1 | 9/2007 |
| WO | 2008/002462 A2 | 1/2008 |
| WO | 2008/036544 A1 | 3/2008 |
| WO | 2008/070198 A2 | 6/2008 |
| WO | 2008/101732 A1 | 8/2008 |
| WO | 2008/147382 A1 | 12/2008 |
| WO | 2009/018473 A1 | 2/2009 |
| WO | 2009/037361 A1 | 3/2009 |
| WO | 2009/105711 A1 | 8/2009 |
| WO | 2010/025302 A2 | 3/2010 |
| WO | 2010/088514 A1 | 8/2010 |
| WO | 2011/094577 A2 | 8/2011 |
| WO | 2012/071069 A1 | 5/2012 |
| WO | 2013/010674 A1 | 1/2013 |
| WO | 2013//052318 A1 | 4/2013 |
| WO | 2014/100732 A1 | 6/2014 |
| WO | 2014/182831 A1 | 11/2014 |
| WO | 2014/182847 A1 | 11/2014 |

OTHER PUBLICATIONS

Huft et al., "Fabrication of High-Quality Microfluidic Solid-Phase Chromatography Columns," *Anal. Chem.* 85:1797-1802, 2013.

Al Zahrani et al., "Accuracy and Utility of Commercially Available Amplification and Serologic Tests for the Diagnosis of Minimal Pulmonary Tuberculosis," *Am J Respir Crit Care Med* 162:1323-1329, 2000.

Aoki et al., "Serine Repeat Antigen (SERA5) is Predominantly Expressed among the Sera Multigene Family of Plasmodium falciparum, and the Acquired Antibody Titers Correlate with Serum Inhibition of the Parasite Growth," *The Journal of Biological Chemistry* 277(49):47533-47540, Dec. 2002.

Arar et al., "Synthesis and Antiviral Activity of Peptide-Oligonucleotide Conjugates Prepared by Using $N_\alpha$-(Bromoacetyl)peptides," *Bioconjugate Chem.* 6(5):573-577, 1995.

Arikan et al., "Anti-Kp 90 IgA Antibodies in the Diagnosis of Active Tuberculosis," *CHEST* 114(5):1253-1257, Nov. 1998.

Birkelund, "The molecular biology and diagnostics of Chlamydia trachomatis," *Danish Medical Bulletin* 39(4):304-320, Aug. 1992.

Bongartz et al., "Improved biological activity of antisense oligonucleotides conjugated to a fusogenic peptide," *Nucleic Acids Research* 22(22):4681-4688, 1994.

Bowden et al., "Using Self-Administered Tampons to Diagnose STDs," *AIDS Patient Care and STDs* 12(1):29-32, 1998.

Carmona et al., "The use of fluorescence resonance energy transfer (FRET) peptides for measurement of clinically important proteolytic enzymes," *An Acad Bras Cienc* 81(3):381-392.

Chan et al., "Polymer surface modification by plasmas and photons," *Surface Science Reports* 24:1-54, 1996.

Chernesky et al., "Clinical Evaluation of the Sensitivity and Specificity of a Commercially Available Enzyme Immunoassay for Detection of Rubella Virus-Specific Immunoglobulin M," *J. Clin. Microbiol.* 20(3):400-404, Sep. 1984.

Chernesky et al., "Detection of Chlamydia trachomatis Antigens by Enzyme Immunoassay and Immunofluorescence in Genital Specimens from Symptomatic and Asymptomatic Men and Women," *The Journal of Infectious Diseases* 154(1):141-148, Jul. 1986.

(56) References Cited

OTHER PUBLICATIONS

Chou et al., "Prevention of pre-PCR mis-priming and primer dimerization improves low-copy-number amplifications," *Nucleic Acids Research* 20(7):1717-1723, 1992.

Crotchfelt et al., "Detection of Neisseria gonorrhoeae and Chlamydia trachomatis in Genitourinary Specimens from Men and Women by a Coamplification PCR Assay," *J. Clin. Microbiol.* 35(6):1536-1540, Jun. 1997.

Cuzzubbo et al., "Use of Recombinant Envelope Proteins for Serological Diagnosis of Dengue Virus Infection in an Immunochromatographic Assay," *Clin. Diagn. Lab. Immunol.* 8(6):1150-1155, 2001.

D'Aquila et al., "Maximizing sensitivity and specificity of PCR by pre-amplification heating," *Nucleic Acids Research* 19(13):3749, 1991.

Dean et al., "Comprehensive human genome amplification using multiple displacement amplification," *PNAS* 99(8):5261-5266, Apr. 2002.

Detter et al., "Isothermal Strand-Displacement Amplification Applications for High-Throughput Genomics," *Genomics* 80(6):691-698, Dec. 2002.

Edelstein et al., "The BARC biosensor applied to the detection of biological warfare agents," *Biosensors & Bioelectronics* 14:805-813, 2000.

Eritja et al., "Synthesis of Defined Peptide-Oligonucleotide Hybrids Containing a Nuclear Transport Signal Sequence," *Tetrahedron* 47(24):4113-4120, 1991.

Fontana et al., "Performance of Strand Displacement Amplification Assay in the Detection of Chlamydia trachomatis and Neisseria gonorrhoeae," *Jpn. J. Infect. Dis.* 58:283-288, 2005.

Frame et al., "Identification and Typing of Herpes Simplex Virus by Enzyme Immunoassay with Monoclonal Antibodies," *J Clin. Microbiol.* 20(2):162-166, Aug. 1984.

Freund et al., (eds.), "Film buckling, bulging, and peeling," in *Thin Film Materials: Stress, Defect Formation and Surface Evolution*, Cambridge, UK, The University of Cambridge, 2003, pp. 312-386.

Gallo et al., "Study of viral integration of HPV-16 in young patients with LSIL," *J Clin Pathol* 56:532-536, 2003.

Garbassi et al., *Polymer Surfaces-From Physics to Technology*, John Wiley and Sons, Baltimore, MD., 1994, pp. 223-241.

Ghai et al., "Identification, expression, and functional characterization of MAEBL, a sporozoite and asexual blood stage chimeric erythrocyte-binding protein of Plasmodium falciparum," *Molecular & Biochemical Parasitology* 123:35-45, 2002.

Gijs, "Magnetic bead handling on-chip: new opportunities for analytical applications," *Microfluid Nanofluid* 1:22-40, 2004.

Gomes et al., "Immunoreactivity and differential developmental expression of known and putative Chlamydia trachomatis membrane proteins for biologically variant serovars representing distinct disease groups," *Microbes and Infection* 7:410-420, 2005.

Graham et al., "Magnetoresistive-based biosensors and biochips," *TRENDS in Biotechnology* 22(9):455-462, Sep. 2004.

Graves et al., "Development of Antibody to Measles Virus Polypeptides During Complicated and Uncomplicated Measles Virus Infections," *Journal of Virology* 49(2):409-412, Feb. 1984.

Grover et al., "Monolithic membrane valves and diaphragm pumps for practical large-scale integration into glass microfluidic devices," *Sensors and Actuators B* 89:315-323, 2003.

Hardt et al., "Passive micromixers for applications in the microreactor and mTAS fields," *Microfluid Nanofluid* 1:108-118, 2005.

Harris et al., "Typing of Dengue Viruses in Clinical Specimens and Mosquitoes by Single-Tube Multiplex Reverse Transcriptase PCR," *J. Clin. Microbiol.* 36(9):2634-2639, Sep. 1998.

Harrison et al., "Synthesis and hybridization analysis of a small library of peptide-oligonucleotide conjugates," *Nucleic Acids Research* 26(13):3136-3145, 1998.

Hummel et al., "Development of quantitative gene-specific real-time RT-PCR assays for the detection of measles virus in clinical specimens," *Journal of Virological Methods* 132:166-173, 2006.

Hung et al., "A specificity enhancer for polymerase chain reaction," *Nucleic Acids Research* 18(16):4953, Jun. 1990.

Innis et al., (eds.), "Optimization of PCRs," in *PCR Protocols: A Guide to Methods and Applications*, Academic Press, Inc., San Diego, California, 1990, pp. 3-12.

Jacobs et al., "Detection of *Streptococcus pneumoniae* Antigen in Bronchoalveolar Lavage Fluid Samples by a Rapid Immunochromatographic Membrane Assay," *J. Clin. Microbiol.* 43(8):4037-4040, 2005.

Joung et al., "Micropumps Based on Alternating High-Gradient Magnetic Fields," *IEEE Transactions on Magnetics* 36(4):2012-2014, Jul. 2000.

Kellogg et al., "TaqStart Antibody: "Hot Start" PCR Facilitated by a Neutralizing Monoclonal Antibody Directed Against Taq DNA Polymerase," *BioTechniques* 16(6):1134-1137, Jun. 1994.

Kennedy et al., "Protein-Protein Coupling Reactions and the Applications of Protein Conjugates," *Clinica Chimica Acta* 70(1):1-31, Jul. 1976.

Khan et al., "Antibiotic Resistance, Virulence Gene, and Molecular Profiles of Shiga Toxin-Producing *Escherichia coli* Isolates from Diverse Sources in Calcutta, India," *J. Clin. Microbiol.* 40(6):2009-2015, Jun. 2002.

Khan et al., "Prevalence and Genetic Profiling of Virulence Determinants of Non-O157 Shiga Toxin-Producing *Escherichia coli* Isolated from Cattle, Beef, and Humans, Calcutta, India," *Emerging Infectious Diseases* 8(1):54-62, Jan. 2002.

Kittigul et al., "Use of a Rapid Immunochromatographic Test for Early Diagnosis of Dengue Virus Infection," *Eur. J. Clin. Microbiol. Infect. Dis.* 21(3):224-226, Mar. 2002.

Knox et al., "Evaluation of Self-Collected Samples in Contrast to Practitioner-Collected Samples for Detection of Chlamydia trachomatis, Neisseria gonorrhoeae, and Trichomonas vaginalis by Polymerase Chain Reaction Among Women Living in Remote Areas," *Sexually Transmitted Diseases* 29(11):647-654, Nov. 2002.

Krasnoperov et al., "Luminescent Probes for Ultrasensitive Detection of Nucleic Acids," *Bioconjug. Chem.* 21(2):319-327, Feb. 2010.

Kremer et al., "Measles Virus Genotyping by Nucleotide-Specific Multiplex PCR," *J. Clin. Microbiol.* 42(7):3017-3022, Jul. 2004.

Kuipers et al., "Detection of Chlamydia trachomatis in peripheral blood leukocytes of reactive arthritis patients by polymerase chain reaction," *Arthritis & Rheumatism* 41(10):1894-1895, Oct. 1998.

Kuipers et al., "Sensitivities of PCR, MicroTrak, ChlamydiaEIA, IDEIA, and PACE 2 for Purified Chlamydia trachomatis Elementary Bodies in Urine, Peripheral Blood, Peripheral Blood Leukocytes, and Synovial Fluid," *J. Clin. Microbiol.* 33(12):3186-3190, Dec. 1995.

Kuno, "Universal diagnostic RT-PCR protocol for arboviruses," *Journal of Virological Methods* 72:27-41, 1998.

Lage et al., "Whole Genome Analysis of Genetic Alterations in Small DNA Samples Using Hyperbranched Strand Displacement Amplification and Array-CGH," *Genome Research* 13:294-307, 2003.

Lanciotti et al., "Rapid Detection and Typing of Dengue Viruses from Clinical Samples by Using Reverse Transcriptase-Polymerase Chain Reaction," *J. Clin. Microbiol.* 30(3):545-551, Mar. 1992.

Leclerc et al., "Meager genetic variability of the human malaria agent Plasmodium vivax," *PNAS* 101(40):14455-14460, Oct. 5, 2004.

Lee et al., "Implementation of Force Differentiation in the Immunoassay," *Analytical Biochemistry* 287:261-271, 2000.

Leung et al., "Rapid antigen detection testing in diagnosing group A b-hemolytic streptococcal pharyngitis," *Expert. Rev. Mol. Diagn.* 6(5):761-766, 2006.

Lindegren et al., "Optimized Diagnosis of Acute Dengue Fever in Swedish Travelers by a Combination of Reverse Transcription-PCR and Immunoglobulin M Detection," *J. Clin. Microbiol.* 43(6):2850-2855, Jun. 2005.

Ling et al., "The Plasmodium falciparum clag9 gene encodes a rhoptry protein that is transferred to the host erythrocyte upon invasion," *Molecular Microbiology* 52(1):107-118, 2004.

Lundquist et al., "Human Recombinant Antibodies against Plasmodium falciparum Merozoite Surface Protein 3 Cloned from Periph-

(56) References Cited

OTHER PUBLICATIONS eral Blood Leukocytes of Individuals with Immunity to Malaria Demonstrate Antiparasitic Properties," *Infect. Immun.* 74(6):3222-3231, Jun. 2006.

Luxton et al., "Use of External Magnetic Fields to Reduce Reaction Times in an Immunoassay Using Micrometer-Sized Paramagnetic Particles as Labels (Magnetoimmunoassay)," *Anal. Chem.* 76(6):1715-1719, Mar. 2004.

Mahony et al., "Chlamydia trachomatis confirmatory testing of PCR-positive genitourinary specimens using a second set of plasmid primers," *Molecular and Cellular Probes* 6:381-388, 1992.

Mahony et al., "Comparison of Plasmid- and Chromosome-Based Polymerase Chain Reaction Assays for Detecting Chlamydia trachomatis Nucleic Acids," *J. Clin. Microbiol.* 31(7):1753-1758, Jul. 1993.

Mahony et al., "Detection of Antichlamydial Immunoglobulin G and M Antibodies by Enzyme-Linked Immunosorbent Assay," *J. Clin. Microbiol.* 18(2):270-275, Aug. 1983.

Mahony et al., "Multiplex PCR for Detection of Chlamydia trachomatis and Neisseria gonorrhoeae in Genitourinary Specimens," *J. Clin. Microbiol.* 33(11):3049-3053, Nov. 1995.

Mahony, "Multiplex Polymerase Chain Reaction for the Diagnosis of Sexually Transmitted Diseases," *Clinics in Laboratory Medicine* 16(0:61-71, Mar. 1996.

Mayta et al., "Use of a reliable PCR assay for the detection of Neisseria gonorrhoeae in Peruvian patients," *Clinical Microbiology and Infection* 12(8): 809-812, Aug. 2006.

Michon et al., "Naturally Acquired and Vaccine-Elicited Antibodies Block Erythrocyte Cytoadherence of the Plasmodium vivax Duffy Binding Protein," *Infect. Immun.* 68(6):3164-3171, Jun. 2000.

Migot-Nabias et al., "Immune Responses Against Plasmodium Falciparum Asexual Blood-Stage Antigens and Disease Susceptibility in Gabonese and Cameroonian Children," *Am. J. Trop. Med. Hyg.* 61(3):488-494, 1999.

Mitrani-Rosenbaum et al., "Simultaneous detection of three common sexually transmitted agents by polymerase chain reaction," *Am J Obstet Gynecol* 171(3):784-790, Sep. 1994.

Mohmmed et al., "Identification of karyopherin b as an immunogenic antigen of the malaria parasite using immune mice and human sera," *Parasite Immunology* 27:197-203, 2005.

Monis et al., "Nucleic acid amplification-based techniques for pathogen detection and identification," *Infection, Genetics and Evolution* 6:2-12, 2006.

Morré et al., "RNA Amplification by Nucleic Acid Sequence-Based Amplification with an Internal Standard Enables Reliable Detection of Chlamydia trachomatis in Cervical Scrapings and Urine Samples," *J. Clin. Microbiol.* 34(12):3108-3114, Dec. 1996.

Narum et al., "A novel Plasmodium falciparum erythrocyte binding protein-2 (EBP2/BAEBL) involved in erythrocyte receptor binding," *Molecular & Biochemical Parasitology* 119:159-168, 2002.

NCBI Database, GenBank Accession No. ACOL01000910, Jun. 9, 2009.

NCBI Database, GenBank Accession No. ACOL01004315, Jun. 9, 2009.

NCBI Database, GenBank Accession No. ACOL01004318, Jun. 9, 2009.

NCBI Database, GenBank Accession No. ACOL01004329, Jun. 9, 2009.

NCBI Database, GenBank Accession No. ACOL01004331, Jun. 9, 2009.

NCBI Database, GenBank Accession No. NP_473155, Jan. 3, 2007.

Nielsen et al., "Detection of Immunoglobulin G Antibodies to Cytomegalovirus Antigens by Antibody Capture Enzyme-Linked Immunosorbent Assay," *J. Clin. Microbiol.* 24(6):998-1003, Dec. 1986.

Oeuvray et al., "Merozoite Surface Protein-3: A Malaria Protein Inducing Antibodies that Promote Plasmodium falciparum Killing by Cooperation With Blood Monocytes," *Blood* 84(5):1594-1602, Sep. 1994.

Ohta et al., "Enzyme-Linked Immunosorbent Assay of Influenza Specific IgA Antibody in Nasal Mucus," *Acta Paediatr Jpn.* 33(5):617-622, Oct. 1991.

Östergaard et al., "A novel approach to the automation of clinical chemistry by controlled manipulation of magnetic particles," *Journal of Magnetism and Magnetic Materials* 194:156-162, 1999.

Ozoemena et al., "Comparative Evaluation of Measles Virus Specific TaqMan PCR and Conventional PCR Using Synthetic and Natural RNA Templates," *Journal of Medical Virology* 73:79-84, 2004.

Park et al., "Polymorphisms of p53, p21 and IRF-1 and cervical cancer susceptibility in Korean Women," *Proceedings of the American Association of Cancer Research* 44, Second Edition, p. 1081, Jul. 2003.

Pfyffer et al., "Diagnostic Performance of Amplified *Mycobacterium tuberculosis* Direct Test with Cerebrospinal Fluid, Other Nonrespiratory, and Respiratory Specimens," *Journal of Clinical Microbiology* 34(4):834-841, Apr. 1996.

Pinder et al., "Immunoglobulin G Antibodies to Merozoite Surface Antigens are Associated with Recovery from Choroquine-Resistant Plasmodium falciparum in Gambian Children," *Infect. Immun.* 74(5):2887-2893, May 2006.

Pingle et al., "Multiplexed Identification of Blood-Borne Bacterial Pathogens by Use of a Novel 16S rRNA Gene PCR-Ligase Detection Reaction-Capillary Electrophoresis Assay," *J. Clin. Microbiol.* 45(6):1927-1935, Jun. 2007.

Polley et al., "Vaccination for vivax malaria: targeting the invaders," *TRENDS in Parasitology* 20(3):99-102, Mar. 2004.

Porstmann et al., "Comparison of Chromogens for the Determination of Horseradish Peroxidase as a Marker in Enzyme Immunoassay," *J. Clin. Chem. Clin. Biochem.* 19(7):435-439, 1981.

Ranjan et al., "Mapping regions containing binding residues within functional domains of Plasmodium vivax and Plasmodium knowlesi erythrocyte-binding proteins," *PNAS* 96(24):14067-14072, Nov. 1999.

Rida et al., "Long-range transport of magnetic microbeads using simple planar coils placed in a uniform magnetostatic field," *Applied Physics Letters* 83(12):2396-2398, Sep. 2003.

Roosendaal et al., "Comparison of different primer sets for detection of Chlamydia trachomatis by the polymerase chain reaction," *J. Med. Microbiol.* 38:426-433, 1993.

Schachter et al., "Ligase Chain Reaction to Detect Chlamydia trachomatis Infection of the Cervix," *J. Clin. Microbiol.* 32(10):2540-2543, Oct. 1994.

Shi et al., "Fabrication and optimization of the multiplex PCR-based oligonucleotide microarray for detection of Neisseria gonorrhoeae, Chlamydia trachomatis and Ureaplasma urealyticum," *Journal of Microbiological Methods* 62:245-256, 2005.

Shi et al., "Natural Immune Response to the C-Terminal 19-Kilodalton Domain of Plasmodium falciparum Merozoite Surface Protein 1," *Infect. Immun.* 64(7):2716-2723, Jul. 1996.

Shu et al., "Development of Group- and Serotype-Specific One-Step SYBR Green I-Based Real-Time Reverse Transcription-PCR Assay for Dengue Virus," *J. Clin. Microbiol.* 41(6):2408-2416, Jun. 2003.

Snounou et al., "High sensitivity of detection of human malaria parasites by the use of nested polymerase chain reaction," *Molecular and Biochemical Parasitology* 61:315-320, 1993.

Soukchareun et al., "Use of Na-Fmoc-cysteine(S-thiobutyl) Derivatized Oligodeoxynucleotides for the Preparation of Oligodeoxynucleotide— Peptide Hybrid Molecules," *Bioconjugate Chem.* 9:466-475, 1998.

Stetsenko et al., "Efficient Conjugation of Peptides to Oligonucleotides by 'Native Ligation'," *J. Org. Chem.* 65:4900-4908, 2000.

Sturm et al., "Vaginal tampons as specimen collection device for the molecular diagnosis of non-ulcerative sexually transmitted infections in antenatal clinic attendees," *International Journal of STD & AIDS* 15:94-98, Feb. 2004.

Tai et al., "Artificial Receptors in Serologic Tests for the Early Diagnosis of Dengue Virus Infection," *Clinical Chemistry* 52(8):1486-1491, 2006.

Tamim et al., "Cervicovaginal coinfections with human papillomavirus and chlamydia trachomatis," *Diagnostic Microbiology and Infectious Disease* 43:277-281, 2002.

(56) References Cited

OTHER PUBLICATIONS

TechNote 303, "Lateral Flow Tests," Bangs Laboratories, Inc., Rev. #002, Apr. 11, 2008, pp. 1-7.

Tongren et al., "Target Antigen, Age, and Duration of Antigen Exposure Independently Regulate Immunoglobulin G Subclass Switching in Malaria," *Infect. Immun.* 74(1):257-264, Jan. 2006.

Trenholme et al., "Antibody Reactivity to Linear Epitopes of Plasmodium Falciparum Cytoadherence-linked asexual gene 9 in asymptomatic children and adults from Papua New Guinea," *Am. J. Trop. Med. Hyg.* 72(6):708-713, 2005.

Tung et al., "Preparation of Applications of Peptide—Oligonucleotide Conjugates," *Bioconjugate Chem*11(5):605-618, Sep./Oct. 2000.

Tung et al., "Preparation of Oligonucleotide-Peptide Conjugates," *Bioconjugate Chem.* 2:464-465, 1991.

Unger et al., "Monolithic Microfabricated Valves and Pumps by Multilayer Soft Lithography," *Science* 288:113-116, Apr. 2000.

van Gemen et al., "Quantifcation of HIV-1 RNA in plasma using NASBAä during HIV-1 primary infection," *Journal of Virological Methods* 43:177-188, 1993.

Van Lintel, "A Piezoelectric Micropump Based on Micromachining of Silicon," *Sensors and Actuators* 15:153-167, 1988.

Vinayagamoorthy et al., "Nucleotide Sequence-Based Multitarget Identification," *J. Clin. Microbiol.* 41(7):3284-3292, Jul. 2003.

Cady, "Quantum dot Molecular Beacons for DNA Detection," in *Micro and Nano Technologies in Bioanalysis*, Lee et al., (eds.), Humana Press, 2009, pp. 367-379.

Cissell et al., "Resonance energy transfer methods of RNA detection," *Analytical and Bioanalytical Chemistry* 393(1):125-135, 2009.

Egger et al., "Reverse Transcription Multiplex PCR for Differentiation between Polio- and Enteroviruses from Clinical and Environmental Samples," *Journal of Clinical Microbiology* 33(6):1442-1447, Jun. 1995.

Franchi et al., "Cations as Mediators of the Adsorption of Nucleic Acids on Clay Surfaces in Prebiotic Environments," *Origins of Life and Evolution of the Biosphere* 33:1-16, Feb. 2003.

Frohman, "Race: Rapid Amplification of cDNA Ends," in *PCR Protocols: A Guide to Methods and Applications*, Innis et al., (eds.), New York, Academic Press, Inc., 1990, pp. 28-38.

Genovese et al., "Virus Variability and Its Impact on HIV and Hepatitis Therapy," *Advances in Virology* 2012:1-3, Dec. 2012.

Kanehisa, "Use of statistical criteria for screening potential homologies in nucleic acid sequences," *Nucleic Acids Research* 12(1):203-213, 1984.

Kwoh et al., "Transcription-based amplification system and detection of amplified human immunodeficiency virus type 1 with a bead-based sandwich hybridization format," *Proc. Natl. Acad. Sci. U.S.A.* 86: 1173-1177, Feb. 1989.

Li et al., "Molecular Beacons: an optimal multifunctional biological probe," *Biochemical and Biophysical Research Communications* 373:457-461, 2008.

Notomi et al., "Loop-mediated isothermal amplification of DNA," *Nucleic Acids Research* 28(12):e63, i-vii, 2000.

Ohara et al., "One-sided polymerase chain reaction: the amplification of cDNA," *Proc. Natl. Acad. Sci. U.S.A.* 86:5673-5677, Aug. 1989.

Staben et al., "Particle transport in Poiseuille flow in narrow channels," *International Journal of Multiphase Flow* 31:529-547, 2005.

Walker et al., "Strand displacement amplification—an insothermal, in vitro DNA amplification technique," *Nucleic Acids Research* 20(7):1691-1696, 1992.

Wang et al., "Molecular engineering of DNA:molecular beacons," *Angew Chem Int Ed Engl* 48(5):856-870, 2009.

Wu et al., "The Ligation Amplification Reaction (LAR)—Amplification of Specific DNA Sequences Using Sequential Rounds of Template-Dependent Ligation," *Genomics* 4:560-569, 1989.

Khanna et al., "Transformation of *Bacillus subtilis* by DNA Bound on Montmorillonite and Effect of DNase on the Transforming Ability of Bound DNA," *Applied and Environmental Microbiology* 58(6):1930-1939, Jun. 1992.

Ramachandran et al., "Dry-reagent storage for disposable lab-on-a-card diagnosis of enteric pathogens," *Proceedings of the 1st Distributed Diagnosis and Home Healthcare (D2H2) Conference*, Arlington, Virginia, USA, Apr. 2-4, 2006, pp. 16-19.

Weigl et al., "Fully integrated multiplexed lab-on-a-card assay for enteric pathogens," *Proc. of SPIE* 6112:611202-1-611202-11, 2006.

Cai et al., "Interactions of DNA with Clay Minerals and Soil Colloidal Particles and Protection Against Degradation by DNase," *Environ Sci. Technol.*40(9):2971-2976, 2006.

\* cited by examiner

METHODS FOR PREPARATION OF NUCLEIC ACID-CONTAINING SAMPLES USING CLAY MINERALS AND ALKALINE SOLUTIONS

STATEMENT OF GOVERNMENT INTEREST

Partial funding of the work described herein was provided by a grant from the U.S. Army Medical Research Acquisition Activity under Contract No. W81XWH-10-2-0158. The U.S. Government has certain rights in this invention.

BACKGROUND

Technical Field

The present invention generally relates to methods for processing samples for molecular diagnostic applications.

Description of the Related Art

Many diagnostic, research, and development procedures require the detection of specific nucleic acid (DNA or RNA) sequences present in a biological sample. For example, nucleic acid detection methods are used to identify bacteria, viruses, or other microorganisms, whose presence can indicate the cause of infectious disease. Nucleic acid biomarkers are the target analytes for several infectious diseases of high global health importance, including human immunodeficiency virus (HIV), Hepatitis C virus (HCV), Hepatitis B virus (HBV), pandemic influenza, and dengue. The nucleic acids of more complex specimens, such as human tissues, are also more and more commonly tested in order to establish the presence of a mutation associated with cancer or a genetic disease. Detection of nucleic acids in samples of biological tissue, such as blood taken directly from a crime scene, is also used to determine the identity of the individual from which the sample originated, as, for example, paternity testing or forensic analysis.

Before a nucleic acid molecule can be detected for any of the purposes noted above, it is necessary to make the specific nucleic acid of interest available from a sample of biological material. The process of releasing nucleic acids from a biological specimen is commonly known in the art as "sample preparation". Frequently, the target nucleic acid will be contained within a viral particle, a bacterial cell, a fungal cell, or the cell of a more complex organism, such as a human white blood cell.

During sample preparation, cells or viral particles may be treated chemically or enzymatically to dissolve or denature the membranes and proteinaceous coats, resulting in release of nucleic acids. This process of dissolution is commonly referred to as "lysis" and the resulting solution containing such lysed material is referred to as a "lysate" or "extract". Unfortunately, such release exposes nucleic acids to degradation by endogenous nucleases present in the sample, which may exist in such abundance that destruction of the nucleic acids begins immediately upon release. Any nucleases remaining during subsequent purification processes can continue to degrade intact nucleic acids, resulting in the loss of the target molecule from the sample. Nucleases are abundant in most biological samples and are often extremely resistant to treatments known to inactivate other enzymes. In particular, ribonucleases (RNases) are active in most, if not all, biological samples, particularly blood, which is the most commonly collected tissue for diagnostic purposes. In addition to nucleases, many other proteins and contaminants are frequently present in biological samples and/or released during preparation of the lysate. For example, blood samples may include heme and heparin (an anti-coagulant used during blood drawing), which interfere with and/or inhibit, many downstream analytic procedures.

To overcome the problem of nucleases and other undesirable products present in biological lysates, it has been necessary to devise complex protocols with steps to both inactivate enzymes and to further purify nucleic acids. For example, anionic detergents and chaotropic agents, such as guanidinium thiocyanate, have been used to simultaneously inactivate or to inhibit nuclease activities while releasing nucleic acids from within cells and subcellular structures. To further purify nucleic acids from lysates, it is common in the art to precipitate the nucleic acids out of the solution, using a low molecular weight alcohol. Because other macromolecules also precipitate under these conditions, producing a sticky, intractable mass that entraps the nucleic acids, it has frequently been necessary to resort to extraction of the sample with hazardous organic solvent mixtures containing phenol, and/or chloroform prior to ethanol precipitation.

A further challenge in preparing samples for RNA analysis is protecting the integrity of these labile molecules. Unlike DNA, RNA is extremely susceptible to hydrolysis. As a consequence, although lysates containing DNA targets can be prepared from biological samples under harsh conditions, preparation of samples for RNA analysis has typically required the use of stabilizing agents, nuclease inhibitors and refrigeration and/or freezing. Variations of two methods have historically been used to prepare RNA from biological samples: chemical extraction and immobilization on glass, often referred to as "solid-phase extraction". As described above, chemical extraction methods usually use highly concentrated chaotropic salts in conjunction with acidic phenol or phenol-chloroform solutions to inactivate RNases and purify RNA from other biomolecules. These methods provide very pure preparations of RNA; however, the RNA must typically be desalted and concentrated with an alcohol precipitation step. The solid-phase extraction method, described in U.S. Pat. No. 5,234,809 to Boom et al., relies on the lysing and nuclease-inactivating properties of the chaotropic agent guanidinium thiocyanate together with the nucleic acid-binding properties of solid-state silica particles or diatoms in the presence of this agent. After silica-bound RNA is washed with a high-salt buffer containing ethanol, the RNA is eluted in a low-ionic-strength buffer.

It will be readily appreciated that sample preparation methods requiring aqueous extraction with organic solvents or chaotropic agents are tedious, hazardous, labor-intensive, and slow. Moreover, if great care is not taken in performing the procedures, residual contamination with nucleases can occur, and the sample nucleic acids will be degraded or lost. Diagnostic tests performed with such samples can give false negative results due to such degradation. False negative results can also be obtained due to chemical interference, for example from residual anionic detergents, chaotropic salts, or ethanol remaining in the sample and inhibiting target amplification procedures. If anionic detergents and proteases have been used, residual proteolytic activity can also degrade the enzymes used in target amplification and/or hybridization detection reactions and produce false negative results. Sample preparation methods based on the "Boom lysis" protocol disclosed in the '809 patent are commonly viewed as adequately addressing these problems. However, the present inventors have unexpectedly found that such extraction methods, utilizing chaotropic salts combined with solid-phase extraction, are not reliably effective in the preparation of blood or plasma samples for PCR-based detection of the HBV genome. Thus, none of the above-cited protocols is suitable for the preparation of a common sample for detection of both DNA and RNA targets from complex biological starting materials, e.g., whole blood and blood serum. This is particularly true for infectious disease diagnosis in clinical laboratory settings, where time demands are very high, and in low-resource areas where cost-effectiveness, reduction of toxic waste streams and simplicity are also of prime importance.

While progress has been made in the field, there continues to be a need in the art for extraction of nucleic acids from various samples and methods for preparation of nucleic acid containing solutions. The present invention fulfills these needs and provides further related advantages.

BRIEF SUMMARY

Embodiments of the present invention provide a sample preparation method that overcomes the drawbacks of the known processes. In particular, it is an object of embodiments of the invention to provide a sample preparation method that enables detection of both DNA and RNA targets from a common sample, such as a biological sample. The present invention offers unprecedentedly rapid, simple, and reproducible methods to provide nucleic acids in such undamaged conditions and with low risk of contamination that such samples can be used immediately as reagents in diagnostic analyses. Embodiments of the present invention are based on a sample preparation method in which samples are treated with a clay mineral prior to extraction or lysis. Then, samples are treated with an alkaline solution to release the nucleic acids from cells or viral particles containing the nucleic acids of interest ("alkaline lysis").

The present inventors have surprisingly found that pretreatment of a sample (e.g., biological sample) with a clay mineral protects nucleic acid molecules, particularly RNA, from hydrolysis during alkaline lysis. Use of a clay mineral according to the methods of the invention also protects nucleic acids from nuclease-mediated degradation. Advantageously, it has been found that a method combining the use of a clay mineral and an alkaline solution enables preparation of a nucleic acid-containing sample sufficiently free of inhibitory and/or degrading enzymes and/or other contaminants that the sample can be used directly for detection assays, such as nucleic acid amplification procedures, without requiring any further purification steps. Embodiments of the present invention thus provide a quick, simple, and relatively non-hazardous method of preparing complex biological samples for detection of both DNA and RNA molecules of interest. The present invention is also particularly suited to miniaturization and compatible with self-contained, "lab-on-a-chip" microfluidic cartridges and other diagnostic test kits and devices. Accordingly, some embodiments are directed to performing the disclosed methods in a microfluidic environment, for example on a microfluidic card.

The present inventors have surprisingly found that a method based on alkaline lysis can be used to prepare complex biological samples for nucleic acid analysis when the method includes treatment of the sample with a clay mineral. The method of the invention can be advantageously used to prepare a common sample for the detection of both DNA and RNA target molecules. The method of the invention offers improvements over known sample preparation methods in that certain embodiments of the present method do not require further purification or isolation of the nucleic acids prior to detection. Without being bound by theory, it is believed that the clay mineral provides several beneficial effects, including, but not limited to: protection of nucleic acids from hydrolysis under alkaline conditions; protection of nucleic acids from nuclease-mediated degradation; protection of downstream assay reagents, such as DNA polymerases, from sample-bound inhibitors and other contaminants; and general buffering properties. The nucleic acid samples prepared according to the present invention are essentially free of nuclease activity and are superior substrates for modifying enzymes. The sample preparation methods disclosed herein are particularly advantageous in the preparation blood or serum samples for the detection of both DNA and RNA viruses. The principal features of the principal embodiments of the present invention are summarized below. Various other objects and advantages of the present invention will be apparent from the detailed description of the invention and the Examples provided herein.

In one embodiment, the present invention relates to a method for treating a nucleic acid-containing sample for analysis of nucleic acids. The method comprises contacting the sample with a clay mineral, mixing the sample and the clay mineral until the clay mineral is evenly dispersed in the sample, substantially removing the clay mineral from the sample, contacting the sample with an alkaline solution at a pH suitable for lysis of cell and viral particles to form a nucleic acid solution, and, optionally, contacting the nucleic acid solution with an acidic solution suitable for neutralizing the pH of the nucleic acid solution. In some embodiments of the foregoing, the sample is a biological sample, for example a solution containing a biological sample.

DETAILED DESCRIPTION

Figure 1:
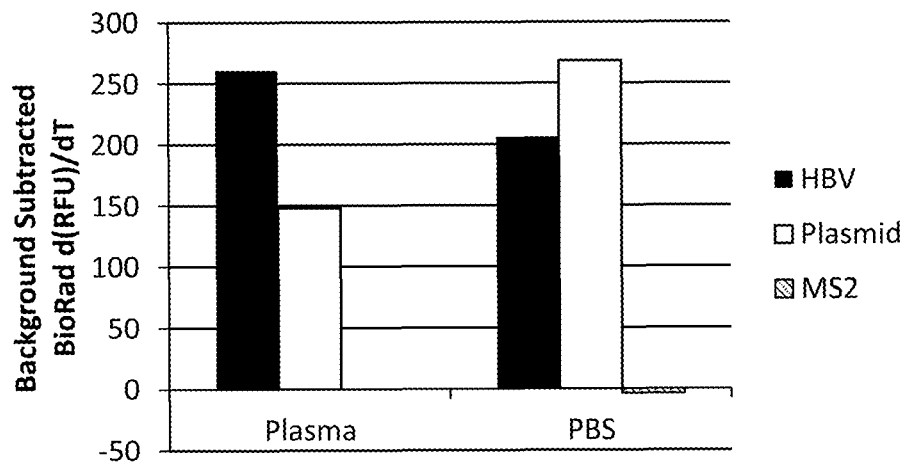
FIG. 1 shows quantitative PCR analysis to detect HBV DNA in samples generated by extracting human plasma containing HBV viral particles under a protocol based on alkaline lysis.

The present invention, in one aspect, is a method of preparing a sample, such as a biological sample, for analysis of both DNA and RNA target molecules using a clay mineral and alkaline lysis. As described herein, "alkaline lysis" refers to use of an alkaline solution to effect the solubilization of microorganism cell walls, viral particles, cellular membranes and/or other structures present in a biological sample. This solubilization of sample constituents is sufficient to release nucleic acids from such structures, making them available for downstream experimental applications. Preferably, a clay mineral is chosen for use in the methods of the present invention that protects the nucleic acids of interest from hydrolysis and nuclease-mediated degradation during alkaline lysis.

Although in a wider sense, the invention is applicable to any nucleic acid-containing starting material, including foods and allied products, vaccines and milk infected with a virus or bacterium, embodiments of the invention are directed to a process in which the starting material employed is a biological material (e.g., biological sample solution) containing an infectious agent, such as a bacterium or viral particle, that contains the nucleic acid of interest. Such infected biological materials include, but are not limited to, whole blood, blood plasma, blood serum, and other bodily fluids, such as urine, sperm, saliva, sputum, respiratory lavages, and tears, and or cellular material such as feces or any other contained on a tissue swab containing the nucleic acids of interest. The biological starting material may also include both normal and cancerous solid tissues, such as lung, colon, pancreas, breast, prostate, and cell cultures (such as mammalian and bacterial cultures) that contain a biomarker of interest.

Accordingly, in various embodiments, the present invention is directed to a method for treating a nucleic acid-containing sample for analysis of nucleic acids, the method comprising the steps of:

a) contacting the sample with a clay mineral;

b) mixing the sample and the clay mineral until the clay mineral is evenly dispersed in the sample;

c) substantially removing the clay mineral from the sample;

d) contacting the sample with an alkaline solution at a pH suitable for lysis of cell and viral particles to form a nucleic acid solution;

e) and, optionally, contacting the nucleic acid solution with an acidic solution suitable for neutralizing the pH of the nucleic acid solution.

In certain embodiments, the sample is a biological sample (e.g., blood, tissue or other sample containing cells). The sample may be provided in various forms, for example as a solution, as a suspension or combinations thereof. In various embodiments the sample is a biological sample solution.

The exact type of clay used in the methods is not particularly limited and can be selected from clays known to one of skill in the art, for example any of the specific clay minerals described herein. In some embodiments, the clay mineral comprises a kaolinite, smectite, or illite clay mineral. In different embodiments, the clay mineral comprises talc. In other embodiments, the clay mineral comprises halloysite. In more embodiments, the clay mineral comprises bentonite. In yet other embodiments, the clay mineral comprises a synthetic clay mineral, for example a laponite.

The alkaline solution is also not particularly limited provided the pH is greater than 7. In some embodiments, the alkaline solution comprises KOH, NaOH, or LiOH, or combinations thereof. In some embodiments, the alkaline solution comprises KOH. In other embodiments, the alkaline solution comprises NaOH. In different embodiments, the alkaline solution comprises LiOH. In various embodiments of the foregoing, the alkaline solution is an aqueous solution of any of the foregoing bases.

Alkaline solutions or buffers are prepared by mixing the alkaline base in a suitable solvent, such as water at a concentration of around 1M. In one embodiment, the alkaline solution or buffer is added at a final concentration of around 0.1M in order to obtain a pH suitable for lysis. It will be appreciated by one of skill in the art that other suitable concentrations may be used in the present invention to achieve effective treatment of the test sample.

Although not required, certain embodiments include an optional neutralizing step for neutralizing the alkaline lysis solution. The neutralizing solution will typically be acidic (i.e., pH less than 7). For example, in some embodiments, the optional acidic solution comprises HCl, $C_2H_4O_2$, or $H_2SO_4$. In some embodiments, the optional acidic solution comprises HCl. In other embodiments, the optional acidic solution comprises $C_2H_4O_2$. In still more embodiments, the optional acidic solution comprises $H_2SO_4$. The optional acidic solution may be provided in the form of an aqueous solution of any suitable acid, for example any of the foregoing acids.

For the optional neutralization step of the present invention, the acidic solution or buffer is added at a concentration sufficient to neutralize the alkaline lysis buffer to around a physiologic pH, such as around pH 7.2. In one embodiment, the acidic buffer or solution is added at a final concentration of around 0.1M.

Any sample which contains a nucleic acid of interest may be used in the presently disclosed methods. In certain embodiments, the sample comprises one or more infectious agents. In certain of these embodiments, the one or more infectious agents are viral agents. In some embodiments, the sample comprises at least two viral agents. For example, in various embodiments, the sample comprises a DNA virus and an RNA virus. In some embodiments, the DNA virus is HBV, and in other embodiments the RNA virus is HCV or HIV.

In some different embodiments, the sample is selected from blood, plasma, serum, urine, saliva, sputum, respiratory lavage, tears, and tissue swabs. In more specific embodiments, the sample is selected from blood, plasma, and serum.

In various different embodiments, the method further comprises a nucleic acid amplification step, for example a nucleic acid amplification step is selected from PCR, RT-PCR, qPCR, and qRT-PCR.

The disclosed methods are suitable for use in any common laboratory format and at various scales. In certain specific embodiments, the methods are performed in a microfluidic card.

The term "nucleic acid" includes polynucleotides and oligonucleotides and refers to a polymeric form of nucleotides of any length, including, but not limited to, ribonucleotides (RNA) and deoxyribonucleotides (DNA). Nucleic acids may be in single-stranded or double stranded or other conformations, or any combination thereof. Relatively short nucleic acid polymers are often used as "primers" or "probes". The definition encompasses nucleic acids from natural sources which can be methylated or capped, and also synthetic forms, which can contain substitute or derivatized nucleobases and may be based on a peptide backbone. Nucleic acids are generally polymers of adenosine, guanine, thymine, and cytosine and their "deoxy-" forms, but may also contain other pyrimidines such as uracil and xanthine, or spacers and universal bases such as deoxyinosine. Deoxynucleic acids may be single-stranded or double-stranded depending on the presence or absence of complementary sequences, and on conditions of pH, salt concentration, temperature, and the presence or absence of certain organic solvents such as formamide, n,n-dimethylformamide, dimethylsulfoxide, and n-methylpyrrolidinone.

"Samples" or "test samples" include any sample which contains a nucleic acid. In various embodiments, the samples are biological samples or "biosamples," which may be clinical specimens. Representative biosamples include, for example: blood, serum, plasma, buffy coat, saliva, wound exudates, pus, lung and other respiratory aspirates, nasal aspirates and washes, sinus drainage, bronchial lavage fluids, sputum, medial and inner ear aspirates, cyst aspirates, cerebral spinal fluid, stool, diarrhoeal fluid, urine, tears, mammary secretions, ovarian contents, ascites fluid, mucous, gastric fluid, gastrointestinal contents, urethral discharge, synovial fluid, peritoneal fluid, meconium, vaginal fluid or discharge, amniotic fluid, semen, penile discharge, or the like may be tested. Assay from swabs or lavages representative of mucosal secretions and epithelia are acceptable, for example mucosal swabs of the throat, tonsils, gingival, nasal passages, vagina, urethra, rectum, lower colon, and eyes, as are homogenates, lysates and digests of tissue specimens of all sorts. Mammalian cells are acceptable samples. Besides physiological or biological fluids, samples of water, industrial discharges, food products, milk, air filtrates, and so forth are also test specimens. In some embodiments, test samples are subjected directly to the disclosed methods; in other embodiments, pre-analytical processing is contemplated.

Target infectious agents particularly suited to the methods of the inventions are microorganisms and viruses with either a DNA-based genome or an RNA-based genome. In some embodiments, suitable viruses include, but are not limited to, Hepatitis B virus (HBV), Hepatitis C virus (HCV), human immunodeficiency viruses (HIV) I and II, influenza A virus, influenza B virus, respiratory syncytial viruses (RSV) A and B, human metapneumovirus (MPV), and herpes simplex viruses (HSV) I and II.

In other embodiments, viral infectious agents which can be detected by the present invention include, but are not limited to, influenza A, influenza B, RSV (respiratory syncytial virus) A and B, human immunodeficiency virus (HIV), human T-cell lymphocytotrophic virus, hepatitis viruses (e.g., Hepatitis B Virus and Hepatitis C Virus), Epstein-Barr Virus, cytomegalovirus, human papillomaviruses, orthomyxo viruses, paramyxo viruses, adenoviruses, corona viruses, rhabdo viruses, polio viruses, toga viruses, bunya viruses, arena viruses, rubella viruses, reo viruses, Norovirus, human metapneumovirus (MPV), Herpes simplex virus 1 and 2 (HSV-1 and HSV-2), West Nile virus, Yellow fever virus, Varicella zoster virus (VZV), Rabies virus, Rhinovirus, Rift Valley fever virus, Marburg virus, mumps virus, measles virus, Epstein-Barr Virus (EBV), human papilloma virus (HPV), Ebola virus, Colorado tick fever virus (CTFV), and/or rhinoviruses.

In different embodiments, bacterial infectious agents which can be detected by the present invention include, but are not limited to, *Escherichia coli, Salmonella, Shigella, Campylobacter, Klebsiella, Pseudomonas, Listeria monocytogenes, Mycobacterium tuberculosis, Mycobacterium avium-intracellulare, Yersinia, Francisella, Pasteurella, Brucella, Clostridia, Bordetella pertussis, Bacteroides, Staphylococcus aureus, Streptococcus pneumonia, B-Hemolytic strep., Corynebacteria, Legionella, Mycoplasma, Ureaplasma, Chlamydia, Clostridium difficile, Gardnerella, Trichomonas vaginalis, Neisseria gonorrhea, Neisseria meningitides, Hemophilus influenza, Enterococcus faecalis, Proteus vulgaris, Proteus mirabilis, Helicobacter pylori, Treponema palladium, Borrelia burgdorferi, Borrelia recurrentis, Rickettsial pathogens, Nocardia, Acitnomycetes* and/or *Acinetobacter*.

In still other embodiments, fungal infectious agents which can be detected by the present invention include, but are not limited to, *Cryptococcus neoformans, Blastomyces dermatitidis, Histoplasma capsulatum, Coccidioides immitis, Paracoccicioides brasiliensis, Candida albicans, Aspergillus fumigautus, Phycomycetes (Rhizopus), Sporothrix schenckii, Chromomycosis,* and/or *Maduromycosis*.

In more embodiments, parasitic agents which can be detected by the present invention include, but are not limited to, *Plasmodium falciparum, Plasmodium malaria, Plasmodium vivax, Plasmodium ovale, Onchoverva volvulus, Leishmania, Trypanosoma* spp., *Schistosoma* spp., *Entamoeba histolytica, Cryptosporidum, Giardia* spp., *Trichomonas* spp., *Balatidium coli, Wuchereria bancrofti, Toxoplasma* spp., *Enterobius vermicularis, Ascaris lumbricoides, Trichuris trichiura, Dracunculus medinesis,* trematodes, *Diphyllobothrium latum, Taenia* spp., *Pneumocystis carinii,* and/or *Necator americanis*.

In general, the term "clay mineral", as used and defined herein, refers to any of a group of hydrous aluminum or magnesium silicates (including phyllosilicates) with a layer (sheet like) structure and very small particle size (customarily less than two micrometers). Clay minerals may contain significant amounts of iron, alkali metals, or alkaline earths. Clay minerals form the main mineral stock of naturally occurring clays and clay stones and are produced from such geologic deposits. Clay minerals may also be derived from other natural sources, such as silt stones, clay slates and some sands and sandstones. Clay minerals may also be produced synthetically.

The term "phyllosilicate", as used and defined herein, includes a broader class of minerals described as sheet silicates, which form parallel sheets of silicate tetrahedra with a composition of $Si_2O_5$ or a 2:5 ratio of silicon to oxygen. Phyllosilicates include the following groups: the serpentine group of antigorite and chrysotile, the apophyllite group, the prehnite group, and the clay mineral groups described below. Any of these phyllosilicates, including the mineral known as talc, is suitable for use in the present invention.

The clay minerals have been classified according to various criteria, including variations of chemical composition. Suitable clay minerals for use in the embodiments disclosed herein include, but are not limited to clays of the following groups: the kaolinite group (e.g., kaolinite, dickite, nacrite, halloysite, hisingerite); the montmorillonite/smectite group (e.g., beidellite, pyrophyllitevermiculite, sauconite, saponite, nontronite and montmorillonite; talc is often, but not always, placed in this group); the illite (or the clay-mica) group (e.g., muscovite, illite); and the chlorite group (e.g., amesite, baileychlore, chamosite, clinochlore, kaemmererite, cookeite, corundophilite, daphnite, delessite, gonyerite, nimite, odinite, orthochamosite, penninite, pannantite, rhipidolite, prochlore, sudoite, thuringite). Other clay minerals suitable in the present invention include albites, phillipsites, analcites, and gibbsites.

Clay minerals are also defined in the art by their atomic structures. Clay minerals formed of a series of 1 tetrahedron and 1 octahedron layer each are referred to as two-layer clay minerals, 1:1 minerals, or as 7 Å clay minerals after the spacing (referred to in the specialist terminology as base spacing), of the tetrahedron layers. This group includes, for example, kaolinite, halloysite, dickite and nacrite. Clay minerals from formations of 1 octahedron and 2 tetrahedron layers are referred to as three-layer, 10 Å minerals, or 2:1 minerals. This group includes, for example, illite and the smectites, glauconite and vermiculite. Montmorillonite is the main representative of the smectite group and the main component of bentonite. In practice bentonite, smectite and montmorillonite are commonly used as synonyms for multilayer silicates. If a further independent octahedron layer is incorporated between the three-layer formations, four-layer, or 14 Å minerals, are produced. A representative of this group is the chlorites. A special clay mineral group is represented by interbedded minerals. Between the layer packages, ions and water molecules can, for example, become embedded. This may lead to an expansion of the layer spacings (swelling), which is commonly observed in the smectites. Any of the clay minerals and clay mineral structures described herein is suitable for the practice of the present invention.

Various types of clay minerals as described herein are available commercially from companies such as Thiele Kaolin Co. (Sandersville, Ga.), Imerys (Roswell, Ga.), Dry Branch Kaolin Co. (Dry Branch, Ga.), Millennium Inorganic Chemicals (Baltimore, Md.), and Minerals Technology Inc. (Specialty Minerals, Bethlehem, Pa.) BYK-Chemie GmbH (Wesel, Germany), Sigma-Aldritch (St. Louis, Mo.), American Colloid Company (Arlington Heights, Ill.).

As noted above, embodiments of the invention are directed to the use of a clay mineral in the preparation of a biological sample for nucleic acid analysis. The clay mineral within the meaning of the invention may be any single clay mineral or a mixture of different clay minerals. According to a particular embodiment, montmorillonite or bentonite is used. Montmorillonite is available under the tradename, MK10. In practice, bentonite, montmorillonite, and smectite are commonly used as synonyms for multi-layer silicates. Montmorillonite is the pure clay mineral. Bentonite is an impure mixture of mostly montmorillonite that may also contain illite and kaolinite. The main types of bentonite are defined by the dominant cation between the sheets of clay: potassium, aluminum, sodium, or calcium. As used here, bentonite contains sodium, but all types of bentonite clays are suitable for the practice of the present invention. According to another embodiment, halloysite is used as a clay mineral. According to yet another embodiment of the invention, Fuller's earth is used as a clay mineral. Fuller's Earth is known in the art as a complex mixture that includes montmorillonites, kaolinites and attapulgites, as well as other minerals like calcite and quartz. According to another embodiment of the invention, the synthetic clay laponite (BYK-Chemie GmbH (Wesel, Germany)), is used as a clay mineral. Whenever mention is made of "a clay mineral" below, this term is also intended to include mixtures of the aforementioned clays.

According to embodiments of the present invention, a sample suspected of containing a nucleic acid of interest is mixed with a clay mineral prior to alkaline lysis treatment. Alkaline buffers are used for the purpose of lysing cells and/or viral particles in the sample to release nucleic acids. For the method of the invention, the presence of a denaturing alkaline base in the buffer is sufficient for lysis of cells and/or viral particles.

In the method of the present invention, a sample, for example a biological sample, suspected of containing nucleic acids of interest is first contacted with a clay mineral. In some embodiments, for example when the sample is a biological sample, the biological sample is in the form of a suspension solution. The method used to suspend a given biological sample in solution will depend upon its nature. Some liquid samples require no further suspension, for example, blood products or urine. In some cases, a liquid solution will require dilution with phosphate-buffered saline (PBS) or similar diluent. Many forms of animal tissue will require more vigorous treatment before being suspended, such as freezing and pulverizing, or by homogenization with a blender or other mechanical mixing device. A suspension solution of this invention is preferably an aqueous solution, and more preferably is an aqueous solution comprising a buffer, even more preferably further comprising an acetate buffer at around pH 6.0

The clay mineral may be dry when contacted with the sample. In cases where the sample is in an aqueous solution, the clay mineral becomes hydrated and suspended in the sample solution. Alternatively, the clay mineral may be hydrated and suspended in an aqueous buffer prior to contact with the sample. In one embodiment of the invention, the aqueous buffer is an acetate buffer at around pH 6.0.

In one embodiment of the invention, the clay mineral is added to a sample solution at a concentration of 20 mg/mL. Other suitable concentrations are contemplated, such as from around 1 mg/mL, 5 mg/mL, 10 mg/mL, 15 mg/mL, 25 mg/mL, 30 mg/mL, 40 mg/mL, 50 mg/mL, 60 mg/mL, 75 mg/mL, 90 mg/mL, 100 mg/mL, 125 mg/mL, 150 mg/mL and up to about 160 mg/mL. It will be appreciated that the amount of clay mineral added to the sample solution will be an amount sufficient to prevent degradation of target nucleic acids and interfere with downstream molecular analyses.

In the method of preparing a sample of this invention, the sample is further mixed with a clay mineral. The mixing step is preferably carried out by incubating the sample and clay mineral at ambient temperature for such a period of time until proteins capable of degrading the nucleic acids in the sample are substantially inactivated. Generally, this will be the amount of time necessary for the clay mineral to become evenly dispersed throughout the sample. In one embodiment of this invention, the sample and clay mineral are mixed for from about five to about 30 minutes. In various embodiments, the clay mineral is mixed with a biological sample, for example a biological sample solution.

In the method of preparing a sample of this invention, the hydrated clay mineral is then substantially removed from the sample. By "substantially removed" it is meant that the amount of residual clay remaining in the sample after removal does not interfere with, or inhibit, the subsequent step(s) of the claimed method. Substantial removal of the clay mineral may be accomplished by well known methods in the art. In one embodiment, the mixed sample may be spun in a microcentrifuge for around two minutes at room temperature to pellet the clay mineral and enable removal of a substantially cleared sample solution. In another embodiment of the invention, the mixed sample may be filtered through a 0.45 µM neutral filter to obtain a sample solution substantially free of clay mineral.

In the method of preparing a sample of this invention, the pH of the clay-treated sample is adjusted to an alkaline pH by adding an alkaline lysis solution. The alkaline lysis solution comprises a base, preferably a base which is sufficiently strong to raise the pH of the solution to a level wherein the structures of the cell membranes and/or viral particles are disrupted (i.e. "lysed") and the nucleic acids of interest are released, but which is not so strong as to damage the nucleic acid material to be isolated. In one embodiment, the base is potassium hydroxide (KOH). In another embodiment, the base is selected from sodium hydroxide (NaOH) or lithium hydroxide (LiOH). Alkaline solutions or buffers are prepared by mixing the alkaline base in water at a concentration of around 1M. In one embodiment, the alkaline solution or buffer is added at a final concentration of around 0.1M and incubated at around room temperature for around 5 and up to around 30 minutes.

The method of the present invention includes an optional neutralization step. Several suitable acids may be used as the optional acidic solution or buffer of the invention. Exemplary acids include hydrochloric acid (HCl) and acetic acid ($C_2H_4O_2$). Acidic solutions or buffers are prepared by mixing the acid with water at a concentration of around 1M. For the optional neutralization step of the present invention, the acidic solution or buffer is added at a concentration sufficient to neutralize the alkaline lysis buffer to around a physiologic pH, such as around pH 7.2. In one embodiment, the acidic buffer or solution is added at a final concentration of around 0.1M.

Nucleic acid containing samples prepared by the methods of the present invention may be used directly in subsequent amplification procedures (PCR-based procedures) without any further purification or isolation steps. A single nucleic acid containing sample prepared by the methods of the present invention may also be used to detect both DNA and RNA target molecules. The general principles and conditions for amplification and detection of nucleic acids using PCR are quite well known, the details of which are provided in numerous references, including U.S. Pat. No. 4,683,195 (Mullis et al.), U.S. Pat. No. 4,683,202 (Mullis), and U.S. Pat. No. 4,965,188 (Mullis et al.), all of which are incorporated herein by reference. Preferably, PCR is carried out using a thermostable DNA polymerase. A number of suitable thermostable DNA polymerases have been reported in the art, including those mentioned in detail in U.S. Pat. No. 4,965,188 (Gelfand et al.) and U.S. Pat. No. 4,889,818 (Gelfand et al.), both incorporated herein by reference in their entireties. Other amplification protocols include LAMP (loop-mediated isothermal amplification of DNA ligase chain reaction ("LCR"), transcription-based amplification systems (TAS), including nucleic acid sequence based amplification (NASBA), "Rolling Circle", "RACE" and "one-sided PCR", also termed "asymmetrical PCR" may also be used, having the advantage that the strand complementary to a detectable probe is synthesized in excess.

In some embodiments, the method for determining the RNA level is an amplification-based method, e.g., by polymerase chain reaction (PCR), especially reverse transcription-polymerase chain reaction (RT-PCR). Prior to the amplification step, a DNA copy (cDNA) of the mRNA must be synthesized. This is achieved by reverse transcription, which can be carried out as a separate step, or in a homogeneous reverse transcription-polymerase chain reaction (RT-PCR), a modification of the polymerase chain reaction for amplifying RNA. Methods suitable for PCR amplification of ribonucleic acids are described by Romero and Rotbart in Diagnostic Molecular Biology: Principles and Applications pp. 401-406; Persing et al., eds., Mayo Foundation, Rochester, Minn., 1993; Egger et al., J. Clin. Microbiol. 33:1442-1447, 1995; and U.S. Pat. No. 5,075,212, all of which are incorporated herein by reference in their entireties.

Assays may include end-point or kinetic (also termed "real time") detection. Where an indicator reagent such as a probe is used, it may be added during amplification or after the amplification. Preferred are fluorescent, fluorescent quenching, and "up-converting" fluorescent probes known in the art.

Quantitation of target nucleic acid levels may be accomplished by real-time quantitative PCR (qPCR) using, for example, the ABI PRISM™ 7600, 7700, or 7900 Sequence Detection System (PE-Applied Biosystems, Foster City, Calif.) according to manufacturer's instructions. Many other suitable detection systems are available, for example, the Qiagen ROTOR-GENE™ and similar systems offered by BioRad. These are fluorescence detection systems, which allows high-throughput quantitation of polymerase chain reaction (PCR) products in real-time. As opposed to standard PCR in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes.

In one embodiment, the fluorescent oligonucleotide probe is a "molecular beacon", a single stranded hairpin-shaped oligonucleotide probe designed to report the presence of specific nucleic acids in a solution. A molecular beacon consists of four components; a stem, hairpin loop, end labelled fluorophore and opposite end-labeled quencher. When the hairpin-like beacon is not bound to a target, the fluorophore and quencher lie close together and fluorescence is suppressed. In the presence of a complementary target nucleotide sequence, the stem of the beacon opens to hybridize to the target. This separates the fluorophore and quencher, allowing the fluorophore to fluoresce. Alternatively, molecular beacons also include fluorophores that emit in the proximity of an end-labelled donor. 'Wavelength-shifting Molecular Beacons' incorporate an additional harvester fluorophore enabling the fluorophore to emit more strongly. Current reviews of molecular beacons include Wang K et al, 2009, Molecular engineering of DNA:molecular beacons. Angew Chem Int Ed Engl, 48(5):856-870; Cissell K A et al, 2009, Resonance energy transfer methods of RNA detection, Anal Bioanal Chem 393(1):125-35 and Li Y, et al, 2008, Molecular Beacons: an optimal multifunctional biological probe, Biochem Biophys Res Comm 373 (4):457-61. Recent advances include Cady N C, 2009, Quantum dot molecular beacons for DNA detection. Methods Mol Biol 554:367-79.

Means for detecting fluorescent signals may include apparatuses well known in the art for displaying an endpoint, i.e., the result of an assay, which may be qualitative or quantitative, and may include a machine equipped with a spectrophotometer, fluorometer, luminometer, photomultiplier tube, photodiode, nephlometer, photon counter, voltmeter, ammeter, pH meter, capacitative sensor, radio-frequency transmitter, magnetoresistometer, or Hall-effect device. Magnifying lenses in the cover plate, optical filters, colored fluids and labeled probes may be used to improve detection and interpretation of assay results.

As used herein, the terms "about", "around", and "generally" are broadening expressions of inexactitude, describing a condition of being "more or less", "approximately", or "almost" in the sense of "just about", where variation would be insignificant, obvious, or of equivalent utility or function, and further indicating that existence of obvious minor exceptions to a norm, rule, or limit. For example, in various embodiments the foregoing terms refer to a quantity within 20%, 10%, 5%, 1% or 0.1% of the value which follows the term.

EXAMPLES

The following Examples are presented in order to provide certain exemplary embodiments of the present invention and are not intended to limit the scope thereof.

Example 1

A Simple Method for Preparing Samples for Detection of Both DNA AND RNA Targets

This example demonstrates a simple and effective method for the preparation of nucleic acids from a biological sample for detection of both DNA and RNA targets.

The present inventors have previously found that nucleic acid extraction protocols based on the use of chaotropic salts, glass/silica substrates, and proteinase K (known in the art as "Boom lysis") are surprisingly ineffective in preparing samples for quantitative polymerase chain reaction (qPCR) detection of Hepatitis B virus (HBV). In order to identify an alternative sample preparation method to detect this DNA virus, a protocol based on alkaline lysis was investigated.

To generate samples for analysis, human plasma was obtained from whole blood collected in a standard purple-topped EDTA collection tube followed by centrifugation at 2000 rpm for 20 minutes to separate plasma from red blood cells. Plasma was then removed and spiked with either HBV or the MS2 RNA phage by adding 50 µL of a HBV of concentration of $1\times10^6$ copies/µL sample of virus to 2 mL of plasma or PBS. Samples were extracted using alkaline lysis by mixing spiked plasma samples with sodium hydroxide (NaOH) at a final concentration of 0.1M for 60 minutes at room temperature. Samples were subsequently neutralized by the addition of 0.1M hydrochloric acid (HCl) and directly used in standard quantitative reverse-transcription polymerase chain reaction (RT-PCR) with a melt analysis to detect viral nucleic acids without any further purification steps. As a control, a plasmid containing an HBV sequence was added to separate samples.

As shown in FIG. 1, alkaline lysis effectively extracted the HBV-spiked sample for PCR analysis, as evidenced by strong PCR signals generated from the plasma and PBS samples spiked with HBV viral particles. In contrast, no signal was generated from the samples spiked with the RNA phage, MS2, indicating that this protocol is not suitable for the preparation of RNA samples. As RNA is susceptible to chemical hydrolysis under alkaline conditions, this result was not surprising.

In order to modify the alkaline lysis protocol to make it suitable for the preparation of RNA targets as well, the effects of treating sample with the aluminum phyllosilicate clay, bentonite, prior to alkaline lysis solution was investigated. Plasma spiked with the MS2 RNA phage was prepared as described above and added to tubes containing bentonite at a final concentration of 20 mg/mL. Samples were mixed until the bentonite clay was thoroughly hydrated with the plasma sample. Samples were incubated for up to 30 minutes then centrifuged to pellet and remove the clay. For alkaline lysis, NaOH was aliquoted to a fresh tube and 50 µL of bentonite-treated plasma to a final concentration of 0.1M. Samples were incubated for 10 minutes then neutralized by the addition of HCl to a final concentration of 0.1M. Samples were directly subjected to qRT-PCR analysis to detect MS2 RNA, without any further nucleic acid purification steps, as described above.

In the absence of clay, phage RNA was not detected in samples prepared by alkaline lysis, as previously observed. Surprisingly, however, pretreatment of samples with bentonite followed by alkaline lysis gave strong PCR signals for the RNA target (not shown). These results indicate that clay protects RNA from hydrolysis in the presence of a strong base.

Figure 2:
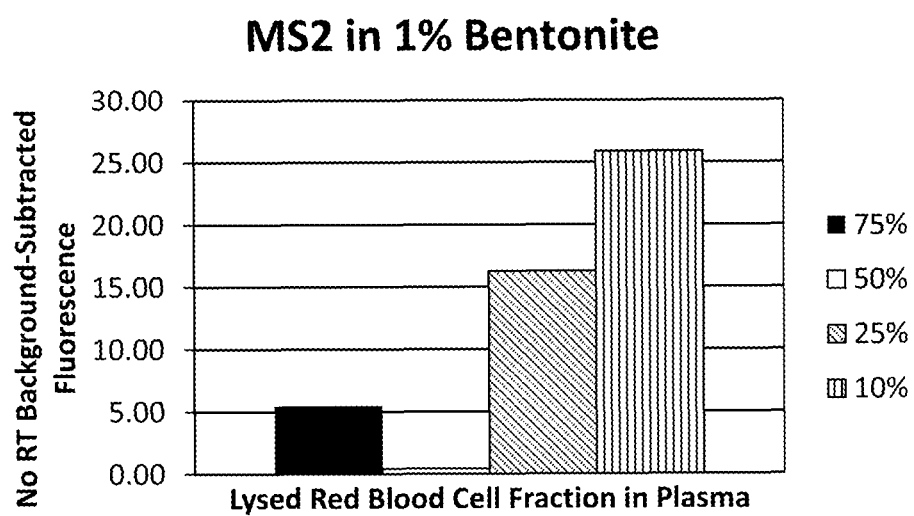
FIG. 2 shows quantitative PCR analysis to detect MS2 RNA in samples generated by extracting human blood containing MS2 RNA under a protocol based on treatment with a clay mineral followed by alkaline lysis.

Next, the bentonite clay/alkaline lysis protocol was tested on whole blood samples collected in EDTA tubes and spiked with the RNA phage, MS2. The particle lysis and PCR analysis procedures were performed as described above on spiked plasma samples containing 10%, 25%, 50%, or 75% lysed red blood cells. As shown in FIG. 2, each sample generated a signal, demonstrating the presence of intact viral RNA in the extracted material. These results indicate that whole blood is a suitable starting material for a sample preparation protocol based on the combination of clay treatment and alkaline lysis. Surprisingly, no further nucleic acid extraction or purification steps are required for detection of an RNA target. Furthermore, while testing various concentrations of base and neutralizing acid in the sample preparation protocol described above, the inventors were surprised to discover that clay-treated samples do not require an acid neutralization step after alkaline lysis and prior to PCR analysis. Without being bound by theory, it is postulated that clay provides certain buffering properties that eliminate the need to add a neutralization step following alkaline lysis.

Example 2

Sample Preparation for DNA and RNA Target Detection Using Alkaline Lysis with Various Clay Minerals This Example demonstrates that a variety of clay minerals are effective in adapting the alkaline lysis protocol to the preparation of samples for detection of both DNA and RNA targets.

In this Example, the following minerals were assessed: the phyllosilicate clays, bentonite, Fuller's earth, and montmorillonite (MK10), and the magnesium silicate, talc. Human plasma samples were prepared as described above and spiked with either the MS2 RNA phage at $10^6$ pfu per sample or the HBV DNA virus at 1,600 or 160 IU/sample. Each clay was added to the plasma sample at a final concentration of 1, 10, 20, or 40 mg/mL and shaken until the clay was thoroughly hydrated (approximately five minutes at room temperature). The clays were removed from the plasma samples by centrifugation, and the samples were subjected to alkaline lysis by adding 1M potassium hydroxide (KOH) to a final concentration of 0.08M at room temperature for 5-10 minutes. No neutralization steps were performed prior to PCR analysis. To test for the presence of viral RNA, standard quantitative RT-PCR analysis was performed on the samples using virus-specific primers.

Figure 3:
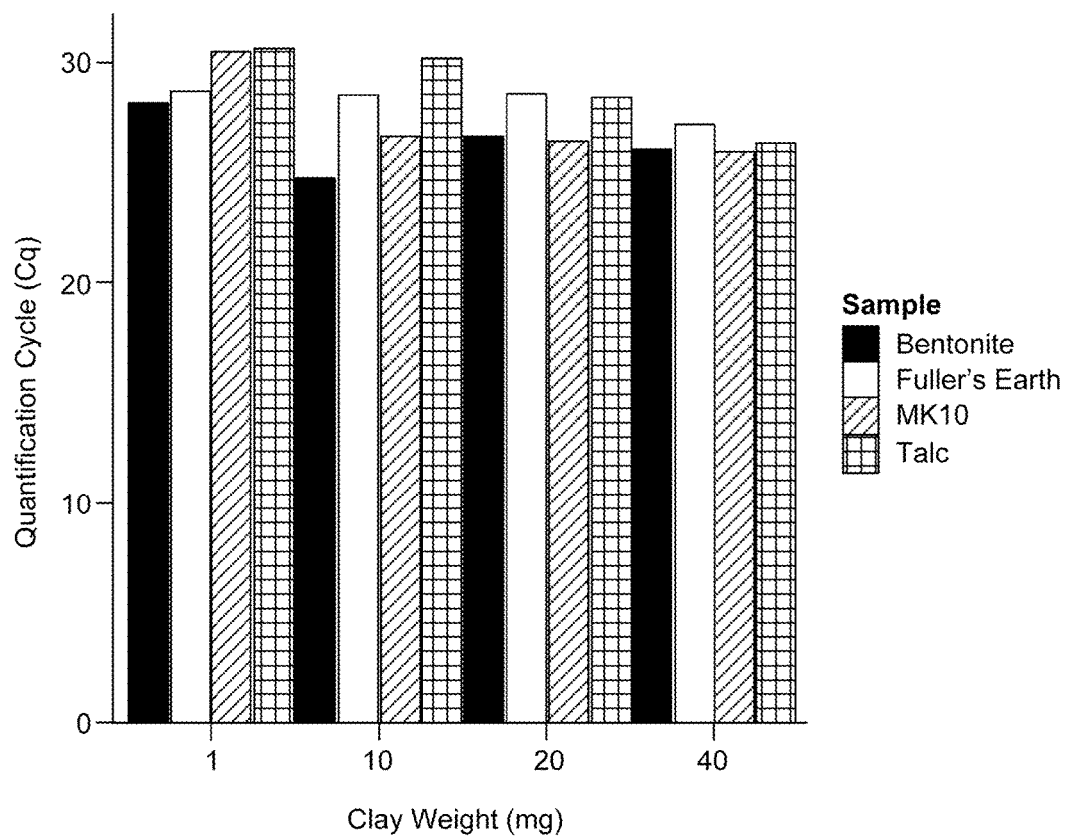
FIG. 3 shows quantitative PCR analysis to detect MS2 RNA in samples generated by extracting human plasma containing MS2 particles under a protocol based on treatment with a clay mineral followed by alkaline lysis.

As shown in FIG. 3, treatment of samples with each of the clay minerals enabled RNA target detection by RT-PCR. In contrast, no viral RNA was detected in the absence of clay treatment. Similar results were obtained when samples were prepared for detection of a DNA target. Here, plasma samples spiked with HBV were subjected to alkaline lysis after pre-treatment with bentonite, halloysite, or bentonite clay screened to ultra-fine particle size (nanobentonite). No further neutralization or purification steps were performed prior to PCR analysis to detect the viral target. These results indicate that several types of clay are suitable to combine with alkaline lysis in order to prepare complex biological samples for nucleic acid analysis.

Example 3

Preparation of a Sample Derived from Whole Blood for Detection of a RNA Target

This Example demonstrates that a sample preparation protocol based on clay lysis can be used to generate an extract of whole blood for the detection of an RNA virus.

It is well known in the art that whole blood contains factors that interfere with PCR analysis. This raises challenges in using unfractionated blood as a sample in nucleic acid-based diagnostic assays. To investigate whether clay may overcome these intrinsic inhibitory properties, whole blood spiked with plasma derived from patients infected with Hepatitis C virus (HCV) was used as a starting material for analysis. In this experiment, either bentonite or the synthetic swelling clay, laponite, was used for sample treatment prior to alkaline lysis. Clay was dissolved in water and added to the HCV-spiked whole blood samples at a final concentration of 0.63-1.33% (wt/vol). Samples were mixed at room temperature for 5-10 minutes and the clay was removed by centrifugation. Samples were subjected to alkaline lysis with KOH as described above. qPCR analysis was performed directly on the lysed whole blood samples without any further extraction or purification steps. The HCV RNA target was detected by standard qRT-PCR using HCV-specific primers and probes.

Figure 4:
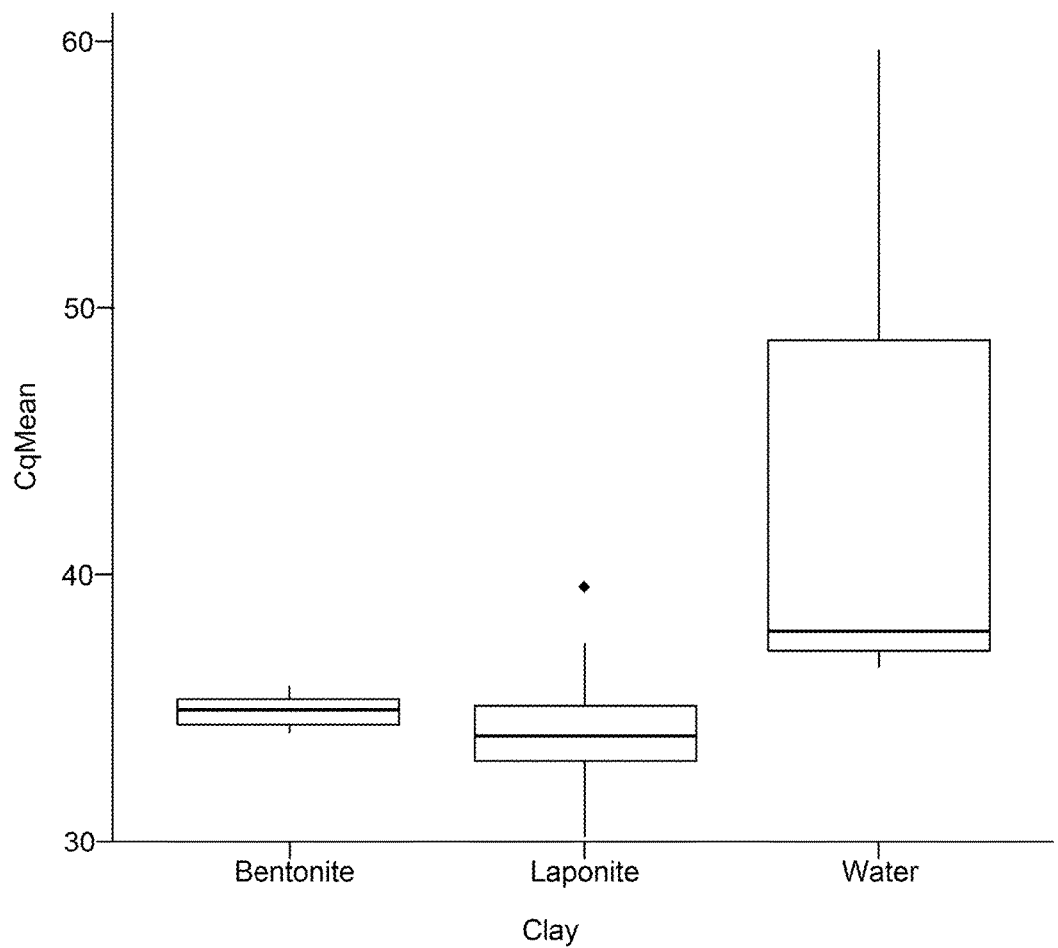
FIG. 4 shows quantitative PCR analysis to detect HCV RNA in samples generated by extracting human blood containing HCV particles under a protocol based on treatment with a clay mineral followed by alkaline lysis.

The PCR data were graphed as box plots of the quantitative cycle (Cq) for each data point, which are set forth in FIG. 4 (lower values of Cq indicate more abundant template and/or a less inhibited qPCR or qRT-PCR)). The boxes represent the interquartile range of the data ("IQR", which is 25-75% of the data points), while the lines through the boxes represents the median value of the data. The whiskers represent the highest and the lowest data points. If the interquartile ranges do not overlap, the data are considered different by a statistically significant margin. As can be seen in FIG. 4, both laponite and bentonite treatment provide a significant improvement in detection of the RNA target in whole blood. These results indicate that clay not only protects the RNA target from alkaline hydrolysis, but also protects the target from nucleases present in whole blood. Furthermore, the data suggest that the combination of clay and alkaline lysis may overcome the inhibitory effects of other factors present in blood on the PCR reaction.

Example 4

Simultaneous DNA and RNA Extraction with Clay and Alkaline Lysis

This Example demonstrates that a protocol based on clay treatment followed by alkaline lysis can be used to prepare a single sample for detection of both a DNA and a RNA target.

In this experiment, human blood was spiked with serum from both a patient infected with HBV and a different patient infected with HCV. The virus-spiked blood samples were pre-treated with bentonite, diatomaceous earth, or laponite clay or no clay as a control. This was followed by alkaline lysis, as described above. Lysed samples were used directly in qRT-PCR reactions without any further extraction or purification steps to detect HBV- or HCV-specific sequences.

Figure 5:
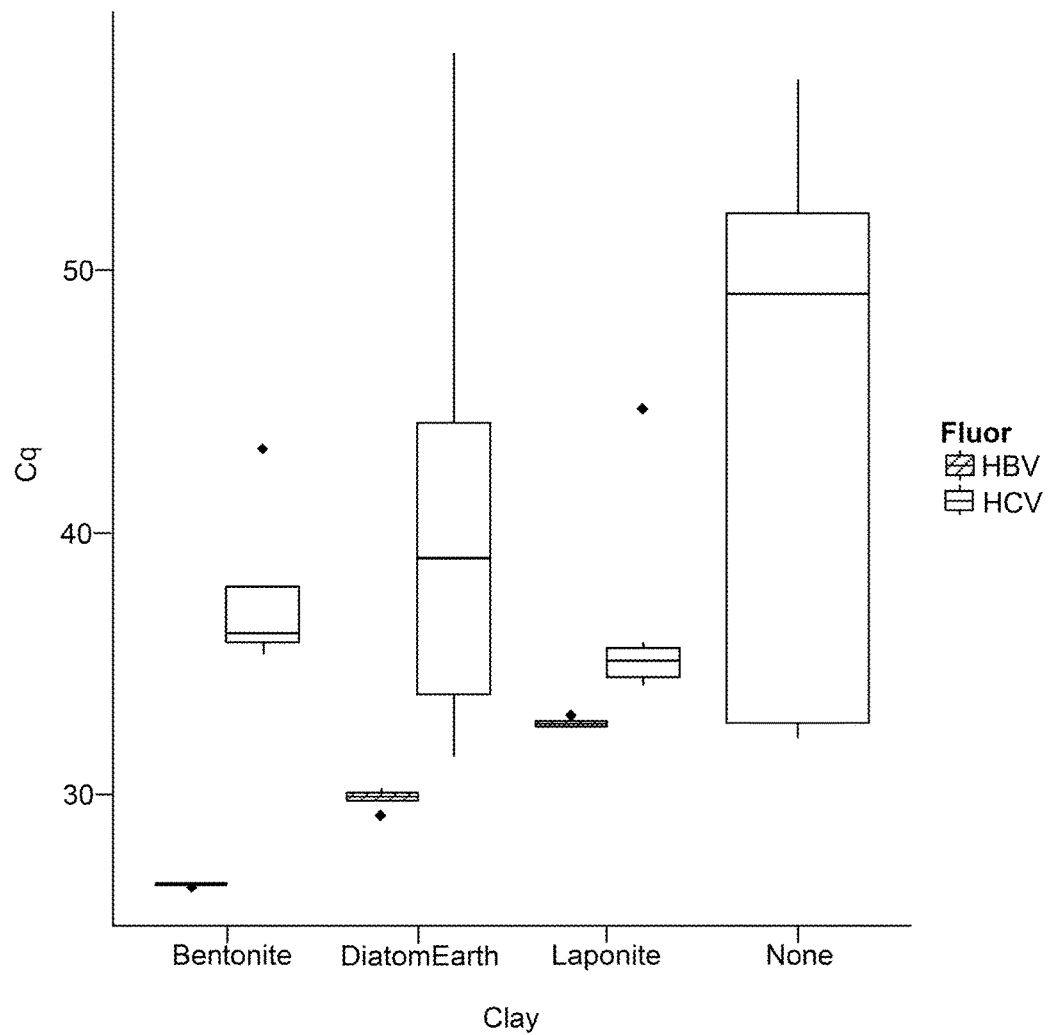
FIG. 5 shows quantitative PCR analysis to detect both HBV DNA and HCV RNA in samples generated by extracting human blood containing HBV and HCV particles under a protocol based on treatment with a clay mineral followed by alkaline lysis.

The Cq data are presented as box plots in FIG. 5, which demonstrate that each of the three clays significantly improves the detection of both RNA and DNA targets present in the same preparation of whole blood sample lysate. Taken together, the data presented in these Examples indicate that clay provides numerous advantageous properties in sample preparation for nucleic acid analysis, including, but not limited to, protection of RNA targets from alkaline hydrolysis and protection of nucleic acid targets and downstream assay components from inhibitors present in biological sample extracts.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, including but not limited to U.S. Patent Application No. 61/820,587, filed May, 7, 2013, are incorporated herein by reference, in their entirety. Aspects of the embodiments can be modified, if necessary to employ concepts of the various patents, applications and publications to provide yet further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method for treating a nucleic acid-containing sample for analysis of nucleic acids, the method comprising the steps of:
   a) contacting the sample with a clay mineral, wherein the clay mineral comprises a kaolinite, a smectite or a synthetic clay mineral and the sample is selected from the group consisting of blood, plasma and serum;
   b) mixing the sample and the clay mineral until the clay mineral is evenly dispersed in the sample;
   c) substantially removing the clay mineral from the sample;
   d) contacting the sample with an alkaline solution at a pH suitable for lysis of cell and viral particles to form a nucleic acid solution; and
   e) optionally, contacting the nucleic acid solution with an acidic solution suitable for neutralizing the pH of the nucleic acid solution.

2. The method of claim 1, wherein the clay mineral comprises a kaolinite, or a smectite clay mineral.

3. The method of claim 1, wherein the clay mineral comprises talc.

4. The method of claim 1, wherein the clay mineral comprises halloysite.

5. The method of claim 1, wherein the clay mineral comprises bentonite.

6. The method of claim 1, wherein the clay mineral comprises a synthetic clay mineral.

7. The method of claim 6, wherein the synthetic clay mineral comprises laponite.

8. The method of claim 1, wherein the alkaline solution comprises KOH, NaOH, or LiOH, or combinations thereof.

9. The method of claim 8, wherein the alkaline solution comprises KOH.

10. The method of claim 1, wherein the pH suitable for lysis is obtained from an alkaline solution of about 0.1 M base.

11. The method of claim 1, wherein the optional acidic solution comprises HCl, $C_2H_4O_2$, or $H_2SO_4$.

12. The method of claim 1, wherein the sample comprises one or more infectious agents.

13. The method of claim 12, wherein the one or more infectious agents are viral agents.

14. The method of claim 13, wherein the sample comprises at least two viral agents.

15. The method of claim 14, wherein the sample comprises a DNA virus and an RNA virus.

16. The method of claim 15, wherein the DNA virus is HBV.

17. The method of claim 16, wherein the RNA virus is HCV or HIV.

18. The method of claim 1, further comprising a nucleic acid amplification step.

19. The method of claim 18, wherein the nucleic acid amplification step is selected from PCR, RT-PCR, qPCR, and qRT-PCR.

\* \* \* \* \*